(12) United States Patent
Seay et al.

(10) Patent No.: US 11,935,629 B2
(45) Date of Patent: Mar. 19, 2024

(54) METHODS FOR FLOW CYTOMETRY PANEL DESIGN BASED ON MODELING AND MINIMIZING SPILLOVER SPREADING, AND SYSTEMS FOR PRACTICING THE SAME

(71) Applicant: Becton, Dickinson and Company, Franklin Lakes, NJ (US)

(72) Inventors: Howard Ray Seay, Medford, OR (US); Aaron Ross, Portland, OR (US); Rane Fields, Portland, OR (US); Peter Mage, San Jose, CA (US); Rick Hou, Portland, OR (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 259 days.

(21) Appl. No.: 17/406,949

(22) Filed: Aug. 19, 2021

(65) Prior Publication Data
US 2022/0108774 A1    Apr. 7, 2022

Related U.S. Application Data

(60) Provisional application No. 63/088,633, filed on Oct. 7, 2020.

(51) Int. Cl.
*G16C 20/64* (2019.01)
*G16C 20/30* (2019.01)
*G16C 20/62* (2019.01)

(52) U.S. Cl.
CPC .......... *G16C 20/64* (2019.02); *G16C 20/30* (2019.02); *G16C 20/62* (2019.02)

(58) Field of Classification Search
USPC .......................................................... 703/12
See application file for complete search history.

(56) References Cited

U.S. PATENT DOCUMENTS

| | | |
|---|---|---|
| 2010/0302536 A1 | 12/2010 | Ball et al. |
| 2011/0204259 A1 | 8/2011 | Rogers et al. |
| 2016/0025621 A1 | 1/2016 | Kapinsky |
| 2018/0231452 A1 | 8/2018 | Ren et al. |
| 2020/0132594 A1 | 4/2020 | Kapinsky |
| 2021/0239592 A1 | 8/2021 | Halpert |
| 2021/0349004 A1 | 11/2021 | Halpert |
| 2021/0404939 A1 | 12/2021 | Hage et al. |
| 2022/0082488 A1 * | 3/2022 | Jaimes ............... G01N 15/0205 |
| 2022/0381671 A1 | 12/2022 | Nishimaki |

FOREIGN PATENT DOCUMENTS

| | | | |
|---|---|---|---|
| AU | 2014228537 A1 | 8/2015 | |
| AU | 2018206722 B2 * | 5/2020 | ............. G01N 15/14 |
| EP | 0774113 | 9/2005 | |
| KR | 20110058715 | 6/2011 | |
| WO | WO2014063247 | 5/2014 | |
| WO | WO2014144826 A1 | 9/2014 | |
| WO | WO2019245709 A1 | 12/2019 | |

OTHER PUBLICATIONS

Nguyen, Richard, et al. "Quantifying spillover spreading for comparing instrument performance and aiding in multicolor panel design." Cytometry Part A 83.3 (2013): 306-315. (Year: 2013).*
Pyne, Saumyadipta, et al. "Automated high-dimensional flow cytometric data analysis." Proceedings of the National Academy of Sciences 106.21 (2009): 8519-8524. (Year: 2009).*
BD Biosciences, "BD Horizon™ Guided Panel Solution (GPS) tool", https://igxorigin.bdbiosciences.com/en-eu/applications/research-applications/multicolor-flow-cytometry/product-selection-tools/horizon-gps-tool, Accessed Jan. 9, 2022, 4 pages.
Chromacyte, "Flow Cytometry Antibodies & Reagents—Antibody Search", www.chromocyte.com, Accessed on Jan. 9, 2022, 2 Pages.
Thermofisher Scientific, "Flow Cytometry Panel Builder", https://www.thermofisher.com/us/en/home/life-science/cell-analysis/flow-cytometry/antibodies-for-flow-cytometry/flow-cytometry-panel-builder.html, Accessed Jan. 10, 2022, 4 Pages.
FluoroFinder, "FluoroFinder Experiment Design Platform", https://fluorofinder.com, Accessed Jan. 9, 2022, 10 Pages.
Chattopadhyay, et al. "Immune monitoring for immuno-oncology applications", The Journal of Immunology, vol. 204, Issue 1, 2020, 5 Pages.
Biolegend, "Multicolor Panel Selector", https://www.biolegend.com/en-us/panel-selector, Accessed Jan. 10, 2022, 3 Pages.
Chattopadhyay, "The Colorful Future of Cell Analysis by Flow Cytometry", Discov Med. . Oct. 2004;4(23):255-62.
Ferrer-Font, et al., "Panel Design and Optimization for High-Dimensional Immunophenotyping Assays Using Spectral Flow Cytometry", Current Protocols in Cytometry, 2020, vol. 92, No. 1, Article No. e70, pp. 1-25.

(Continued)

*Primary Examiner* — G. Steven Vanni
(74) *Attorney, Agent, or Firm* — Khin K. Chin; Bret E. Field; BOZICEVIC, FIELD & FRANCIS LLP

(57) ABSTRACT

Aspects of the present disclosure include methods for identifying a set of fluorophore-biomolecule reagent pairs for characterizing a sample by flow cytometry. Methods according to certain embodiments include calculating a spectral spillover spreading parameter for a plurality of fluorophores, pairing each fluorophore with a biomolecule that is specific for a biomarker of a cell in the sample to generate a plurality of fluorophore-biomolecule reagent pairs, generating an adjusted spillover spreading matrix for the fluorophore-biomolecule reagent pairs based on the spectral spillover spreading parameter of each fluorophore and a biomarker classification parameter and identifying an optimal set of fluorophore-biomolecule reagent pairs based on the calculated spillover spreading values from the adjusted spillover spreading matrix. Systems and non-transitory computer readable storage medium for practicing the subject methods are also provided.

15 Claims, 7 Drawing Sheets

(2 of 7 Drawing Sheet(s) Filed in Color)

(56) References Cited

OTHER PUBLICATIONS

Isac, "Data File Standard for Flow Cytometry—Version 4.0", 2016, 69 Pages.
Panelbuilder, http://angularjs.org, Downloaded Oct. 28, 2021, 2429 Pages.
Thermo Fisher Scientific, "Flow Cytometry Panel Builder", www.thermofisher.com/us/en/home.html, Downloaded May 3, 2023, 3 pages.
Thermo Fisher Scientific, "Flow Cytometry Panel Builder", www.thermofisher.com/us/en/home.html, Downloaded May 3, 2023, 4 pages.

* cited by examiner

METHODS FOR FLOW CYTOMETRY PANEL DESIGN BASED ON MODELING AND MINIMIZING SPILLOVER SPREADING, AND SYSTEMS FOR PRACTICING THE SAME

CROSS-REFERENCE TO RELATED APPLICATION

Pursuant to 35 U.S.C. § 119 (e), this application claims priority to the filing dates of U.S. Provisional Patent Application Ser. No. 63/088,633 filed Oct. 7, 2020, the disclosure of which application is incorporated herein by reference in their entirety.

INTRODUCTION

Flow cytometry is a technique used to characterize biological material, such as cells of a blood sample or particles of interest in another type of biological or chemical sample. A flow cytometer typically includes a sample reservoir for receiving a fluid sample, such as a blood sample, and a sheath reservoir containing a sheath fluid. The flow cytometer transports the particles (including cells) in the fluid sample as a cell stream to a flow cell, while also directing the sheath fluid to the flow cell. To characterize the components of the flow stream, the flow stream is irradiated with light. Variations in the materials in the flow stream, such as morphologies or the presence of fluorescent labels, may cause variations in the observed light and these variations allow for characterization and separation. For example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components may be simultaneously detected by using spectrally distinct fluorescent dyes to label the different particles or components. In some implementations, a multiplicity of detectors, one for each of the scatter parameters to be measured, and one or more for each of the distinct dyes to be detected are included in the analyzer. For example, some embodiments include spectral configurations where more than one sensor or detector is used per dye. The data obtained include the signals measured for each of the light scatter detectors and the fluorescence emissions.

SUMMARY

Aspects of the present disclosure include methods for identifying a set of fluorophore-biomolecule reagent pairs for characterizing a sample by flow cytometry. Methods according to certain embodiments include calculating a spectral spillover spreading parameter for a plurality of fluorophores, pairing each fluorophore with a biomolecule that is specific for a biomarker of a cell in the sample to generate a plurality of fluorophore-biomolecule reagent pairs, generating an adjusted spillover spreading matrix for the fluorophore-biomolecule reagent pairs based on the spectral spillover spreading parameter of each fluorophore and a biomarker classification parameter and identifying an optimal set of fluorophore-biomolecule reagent pairs based on the calculated spillover spreading values from the adjusted spillover spreading matrix. Systems and non-transitory computer readable storage medium for practicing the subject methods are also provided.

In practicing the subject methods, a spectral spillover spreading parameter is calculated for a plurality of fluorophores. In some embodiments, calculating the spectral spillover spreading parameter includes generating a matrix of fluorescence spillover spreading values for the plurality of fluorophores. In embodiments, the fluorescence spillover spreading values in the matrix are calculated based on the fluorescence spillover spread of a fluorophore when in the presence of another fluorophore. In some embodiments, the fluorescence spillover spreading value is calculated based on the overlap of the fluorescence spectra of the two different fluorophores. In some instances, calculating the spectral spillover spreading parameter includes calculating a sum of each row of the generated matrix. In certain instances, the sum of each row of the generated matrix is an approximation of the spectral spillover spread by each individual fluorophore into the plurality of fluorophores. In other instances, calculating the spectral spillover spreading parameter includes calculating a sum of each column of the generated matrix. In certain instances, the sum of each column of the generated matrix is an approximation of the spectral spillover spread by the plurality of fluorophores into each other individual fluorophore. In certain embodiments, the spectral spillover spreading parameter for each of the plurality of fluorophores is simulated. Where the spectral spillover spreading parameter is calculated by simulation, methods may include simulating spectral properties of each fluorophore and calculating spillover spreading values for each of the fluorophores based on the simulated spectral properties. For example, the simulated spectral properties of the fluorophore may be one or more of emission spectrum of the fluorophore, excitation spectrum of the fluorophore, quantum yield of the fluorophore and extinction coefficient of the fluorophore. The spillover spreading values for each of the fluorophores may be calculated, in some embodiments, by compensation. In other embodiments, the spillover spreading values for each of the fluorophores is calculated by spectral unmixing.

Each fluorophore is paired with a biomolecule that is specific for a biomarker of a cell in the sample. The biomolecule may be a polypeptide, a nucleic acid or a polysaccharide. In certain embodiments, the biomolecule is a nucleic acid, such as an oligonucleotide, DNA or RNA. In other embodiments, the biomolecule is a polypeptide, such as a protein, an enzyme or an antibody. In embodiments, methods include calculating an adjusted spillover spreading matrix for the fluorophore-biomolecule reagent pairs based on the spectral spillover spreading parameter (measured by experiment or simulated) of each fluorophore and a biomarker classification parameter. In some embodiments, the biomarker classification parameter includes a quantitative population density component for each biomarker in the sample. In some instances, the quantitative population density is a numerical range of the population of each biomarker in the sample. In other instances, the biomarker classification parameter is a semi-quantitative population density classification for each biomarker in the sample. For example, the semi-quantitative population density classification may be a designation of biomarker expression, such as where the designation of biomarker expression is 1) very high biomarker expression; 2) high biomarker expression; 3) medium biomarker expression; 4) low biomarker expression and 5) absent biomarker expression. In yet other instances, the biomarker classification parameter includes a qualitative population density classification for each biomarker in the sample. In certain instances, the qualitative population density classification for each biomarker in the sample is a binary biomarker classification. In one example, the binary biomarker classification may be a designation according to whether a biomarker is present or absent. In another example, the binary biomarker classification may be a designation according to whether a biomarker is expected to be present in the sample above a predetermined threshold (e.g., a minimum antigen density). In yet another example, the binary biomarker classification may be a designation of the criticality of the biomarker to identified set of fluorophore-biomolecule reagent pairs. For instances, the binary biomarker classification may be a designation of a biomarker as being 1) critical or 2) non-critical to the identified set of fluorophore-biomolecule reagent pairs.

In practicing the subject methods, the calculated adjusted spillover spreading matrix for the plurality of fluorophore-biomolecule reagent pairs is used to identify an optimal set of fluorophore-biomolecule reagent pairs for characterizing the sample by flow cytometry. In some embodiments, identifying the optimal set of fluorophore-biomolecule reagent pairs includes a reagent pair ranking algorithm, such as where each of the fluorophore-biomolecule reagent pairs is assigned a score based on the calculated adjusted spillover spreading matrix value for each fluorophore-biomolecule reagent pair. In some embodiments, identifying the optimal set of fluorophore-biomolecule reagent pairs includes selecting the fluorophore-biomolecule reagent pairs having the lowest score based on the calculated adjusted spillover spreading matrix. In other embodiments, identifying the optimal set of fluorophore-biomolecule reagent pairs includes selecting the fluorophore-biomolecule reagent pairs having a score that is below a predetermined threshold based on the calculated adjusted spillover spreading matrix. In yet other embodiments, identifying the optimal set of fluorophore-biomolecule reagent pairs includes selecting at random a predetermined number of the fluorophore-biomolecule reagent pairs. In other embodiments, identifying the optimal set of fluorophore-biomolecule reagent pairs includes applying a constrained optimization algorithm, such as where each fluorophore-biomolecule reagent pair is selected at random and subjected to a set of constraints to generate a constrained set of fluorophore-biomolecule reagent pairs. In certain embodiments, the constrained optimization algorithm includes a constraint conflict algorithm. In certain instances, the constraint conflict algorithm is an iterative minimal conflict algorithm. In other embodiments, the constrained optimization algorithm includes a constraint satisfaction algorithm. In certain embodiments, identifying the optimal set of fluorophore-biomolecule reagent pairs includes applying an iterative genetic algorithm.

Systems for practicing the subject methods are also provided. Systems according to certain embodiments include a processor having memory operably coupled to the processor where the memory includes instructions stored thereon, which when executed by the processor, cause the processor to: calculate a spectral spillover spreading parameter for a plurality of fluorophores, pair each fluorophore with a biomolecule that is specific for a biomarker of a cell in the sample to generate a plurality of fluorophore-biomolecule reagent pairs, generate an adjusted spillover spreading matrix for the fluorophore-biomolecule reagent pairs based on the spectral spillover spreading parameter of each fluorophore and a biomarker classification parameter and identify an optimal set of fluorophore-biomolecule reagent pairs based on the calculated spillover spreading values from the adjusted spillover spreading matrix.

In embodiments, systems include a processor with memory having instructions stored thereon, which when executed by the processor, cause the processor to calculate a spectral spillover spreading parameter for a plurality of fluorophores. In some embodiments, the memory includes instructions for calculating the spectral spillover spreading parameter by generating a matrix of fluorescence spillover spreading values for the plurality of fluorophores. Systems include memory having instructions where the fluorescence spillover spreading values in the matrix are calculated based on the fluorescence spillover spread of a fluorophore when in the presence of another fluorophore. In some embodiments, the memory includes instructions for calculating the fluorescence spillover spreading value based on the overlap of the fluorescence spectra of the two different fluorophores. In some instances, the memory includes instructions for calculating the spectral spillover spreading parameter by calculating a sum of each row of the generated matrix. In certain instances, the sum of each row of the generated matrix is an approximation of the spectral spillover spread by each individual fluorophore into the plurality of fluorophores. In other instances, the memory includes instructions for calculating the spectral spillover spreading parameter by calculating a sum of each column of the generated matrix. In certain instances, the sum of each column of the generated matrix is an approximation of the spectral spillover spread by the plurality of fluorophores into each other individual fluorophore.

In certain embodiments, the memory includes instructions stored thereon, which when executed by the processor, cause the processor to simulate the spectral spillover spreading parameter for each of the plurality of fluorophores. In some embodiments, the memory includes instructions for simulating spectral properties of each fluorophore and instructions for calculating spillover spreading values for each of the fluorophores based on the simulated spectral properties. For example, the simulated spectral properties of the fluorophore may be one or more of emission spectrum of the fluorophore, excitation spectrum of the fluorophore, quantum yield of the fluorophore and extinction coefficient of the fluorophore. In certain embodiments, the memory includes instruction for calculating the spillover spreading values for each of the fluorophores by compensation. In other embodiments, the memory includes instruction for calculating the spillover spreading values for each of the fluorophores by spectral unmixing.

In embodiments, the systems includes memory having instructions stored thereon, which when executed by the processor, cause the processor to pair each fluorophore with a biomolecule that is specific for a biomarker of a cell in the sample. In some embodiments, the memory includes instructions for calculating an adjusted spillover spreading matrix for the fluorophore-biomolecule reagent pairs based on the spectral spillover spreading parameter of each fluorophore and a biomarker classification parameter. In some embodiments, the biomarker classification parameter includes a quantitative population density component for each biomarker in the sample. In some instances, the quantitative population density is a numerical range of the population of each biomarker in the sample. In other instances, the biomarker classification parameter is a semi-quantitative population density classification for each biomarker in the sample. For example, the semi-quantitative population density classification may be a designation of biomarker expression, such as where the designation of biomarker expression is 1) very high biomarker expression; 2) high biomarker expression; 3) medium biomarker expression; 4) low biomarker expression and 5) absent biomarker expression. In yet other instances, the biomarker classification parameter includes a qualitative population density classification for each biomarker in the sample. In certain instances, the qualitative population density classification for each biomarker in the sample is a binary biomarker classification. In one example, the binary biomarker classification may be a designation according to whether a biomarker is present or absent. In another example, the binary biomarker classification may be a designation according to whether a biomarker is expected to be present in the sample above a predetermined threshold (e.g., a minimum antigen density). In yet another example, the binary biomarker classification may be a designation of the criticality of the biomarker to identified set of fluorophore-biomolecule reagent pairs. For instances, the binary biomarker classification may be a designation of a biomarker as being 1) critical or 2) non-critical to the identified set of fluorophore-biomolecule reagent pairs.

Systems of interest include memory having instructions stored thereon, which when executed by the processor, cause the processor to identify an optimal set of fluorophore-biomolecule reagent pairs for characterizing the sample by flow cytometry. In some embodiments, the memory includes instructions for identifying the optimal set of fluorophore-biomolecule reagent pairs with a reagent pair ranking algorithm, such as where the memory includes instructions for assigning a score to each of the fluorophore-biomolecule reagent pairs based on the calculated adjusted spillover spreading matrix value for each fluorophore-biomolecule reagent pair. In some embodiments, the memory includes instructions for identifying the optimal set of fluorophore-biomolecule reagent pairs by selecting the fluorophore-biomolecule reagent pairs having the lowest score based on the calculated adjusted spillover spreading matrix. In other embodiments, the memory includes instructions for identifying the optimal set of fluorophore-biomolecule reagent pairs by selecting the fluorophore-biomolecule reagent pairs having a score that is below a predetermined threshold based on the calculated adjusted spillover spreading matrix. In yet other embodiments, the memory includes instructions for identifying the optimal set of fluorophore-biomolecule reagent pairs by selecting at random a predetermined number of the fluorophore-biomolecule reagent pairs.

In other embodiments, systems include memory having instructions for identifying the optimal set of fluorophore-biomolecule reagent pairs by applying a constrained optimization algorithm, such as where each fluorophore-biomolecule reagent pair is selected at random and subjected to a set of constraints to generate a constrained set of fluorophore-biomolecule reagent pairs. In certain embodiments, the constrained optimization algorithm implemented by the memory of the subject system includes a constraint conflict algorithm. In certain instances, the constraint conflict algorithm is an iterative minimal conflict algorithm. In other embodiments, the constrained optimization algorithm includes a constraint satisfaction algorithm. In certain embodiments, the memory includes instructions for identifying the optimal set of fluorophore-biomolecule reagent pairs by applying an iterative genetic algorithm.

Non-transitory computer readable storage medium for identifying a set of fluorophore-biomolecule reagent pairs for characterizing a sample by flow cytometry are also provided. Non-transitory computer readable storage medium according to certain embodiments include instructions stored thereon having algorithm for calculating a spectral spillover spreading parameter for a plurality of fluorophores, algorithm for pairing each fluorophore with a biomolecule that is specific for a biomarker of a cell in the sample to generate a plurality of fluorophore-biomolecule reagent pairs, algorithm for generating an adjusted spillover spreading matrix for the fluorophore-biomolecule reagent pairs based on the spectral spillover spreading parameter of each fluorophore and a biomarker classification parameter and algorithm for identifying an optimal set of fluorophore-biomolecule reagent pairs based on the calculated spillover spreading values from the adjusted spillover spreading matrix.

In embodiments, the non-transitory computer readable storage medium includes algorithm for calculating a spectral spillover spreading parameter for a plurality of fluorophores. In some embodiments, the non-transitory computer readable storage medium includes algorithm for calculating the spectral spillover spreading parameter by generating a matrix of fluorescence spillover spreading values for the plurality of fluorophores. Non-transitory computer readable storage medium include algorithm for calculating the fluorescence spillover spreading values in the matrix based on the fluorescence spillover spread of a fluorophore when in the presence of another fluorophore. In some embodiments, the non-transitory computer readable storage medium includes algorithm for calculating the fluorescence spillover spreading value based on the overlap of the fluorescence spectra of the two different fluorophores. In some instances, the non-transitory computer readable storage medium includes algorithm for calculating the spectral spillover spreading parameter by calculating a sum of each row of the generated matrix. In certain instances, the sum of each row of the generated matrix is an approximation of the spectral spillover spread by each individual fluorophore into the plurality of fluorophores. In other instances, the non-transitory computer readable storage medium includes algorithm for calculating the spectral spillover spreading parameter by calculating a sum of each column of the generated matrix. In certain instances, the sum of each column of the generated matrix is an approximation of the spectral spillover spread by the plurality of fluorophores into each other individual fluorophore.

In certain embodiments, the non-transitory computer readable storage medium includes algorithm for simulating the spectral spillover spreading parameter for each of the plurality of fluorophores. In some embodiments the non-transitory computer readable storage medium includes algorithm for simulating spectral properties of each fluorophore and algorithm for calculating spillover spreading values for each of the fluorophores based on the simulated spectral properties. For example, the simulated spectral properties of the fluorophore may be one or more of emission spectrum of the fluorophore, excitation spectrum of the fluorophore, quantum yield of the fluorophore and extinction coefficient of the fluorophore. In certain embodiments, the non-transitory computer readable storage medium includes algorithm for calculating the spillover spreading values for each of the fluorophores by compensation. In other embodiments, the non-transitory computer readable storage medium includes algorithm for calculating the spillover spreading values for each of the fluorophores by spectral unmixing.

In embodiments, the non-transitory computer readable storage medium includes algorithm for pairing each fluorophore with a biomolecule that is specific for a biomarker of a cell in the sample. In some embodiments, the non-transitory computer readable storage medium includes algorithm for calculating an adjusted spillover spreading matrix for the fluorophore-biomolecule reagent pairs based on the spectral spillover spreading parameter of each fluorophore and a biomarker classification parameter. In some embodiments, the biomarker classification parameter includes a quantitative population density component for each biomarker in the sample. In some instances, the quantitative population density is a numerical range of the population of each biomarker in the sample. In other instances, the biomarker classification parameter is a semi-quantitative population density classification for each biomarker in the sample. For example, the semi-quantitative population density classification may be a designation of biomarker expression, such as where the designation of biomarker expression is 1) very high biomarker expression; 2) high biomarker expression; 3) medium biomarker expression; 4) low biomarker expression and 5) absent biomarker expression. In yet other instances, the biomarker classification parameter includes a qualitative population density classification for each biomarker in the sample. In certain instances, the qualitative population density classification for each biomarker in the sample is a binary biomarker classification. In one example, the binary biomarker classification may be a designation according to whether a biomarker is present or absent. In another example, the binary biomarker classification may be a designation according to whether a biomarker is expected to be present in the sample above a predetermined threshold (e.g., a minimum antigen density). In yet another example, the binary biomarker classification may be a designation of the criticality of the biomarker to identified set of fluorophore-biomolecule reagent pairs. For instance, the binary biomarker classification may be a designation of a biomarker as being 1) critical or 2) non-critical to the identified set of fluorophore-biomolecule reagent pairs.

The non-transitory computer readable storage medium includes algorithm for identifying an optimal set of fluorophore-biomolecule reagent pairs for characterizing the sample by flow cytometry. In some embodiments, the non-transitory computer readable storage medium includes algorithm for identifying the optimal set of fluorophore-biomolecule reagent pairs with a reagent pair ranking algorithm, such as where the non-transitory computer readable storage medium includes algorithm for assigning a score to each of the fluorophore-biomolecule reagent pairs based on the calculated adjusted spillover spreading matrix value for each fluorophore-biomolecule reagent pair. In some embodiments, the non-transitory computer readable storage medium includes algorithm for identifying the optimal set of fluorophore-biomolecule reagent pairs by selecting the fluorophore-biomolecule reagent pairs having the lowest score based on the calculated adjusted spillover spreading matrix. In other embodiments, the non-transitory computer readable storage medium includes algorithm for identifying the optimal set of fluorophore-biomolecule reagent pairs by selecting the fluorophore-biomolecule reagent pairs having a score that is below a predetermined threshold based on the calculated adjusted spillover spreading matrix. In yet other embodiments, the non-transitory computer readable storage medium includes algorithm for identifying the optimal set of fluorophore-biomolecule reagent pairs by selecting at random a predetermined number of the fluorophore-biomolecule reagent pairs.

In other embodiments, the non-transitory computer readable storage medium includes algorithm for identifying the optimal set of fluorophore-biomolecule reagent pairs by applying a constrained optimization algorithm, such as where each fluorophore-biomolecule reagent pair is selected at random and subjected to a set of constraints to generate a constrained set of fluorophore-biomolecule reagent pairs. In certain embodiments, the constrained optimization algorithm includes a constraint conflict algorithm. In certain instances, the constraint conflict algorithm is an iterative minimal conflict algorithm. In other embodiments, the constrained optimization algorithm includes a constraint satisfaction algorithm. In certain embodiments, the non-transitory computer readable storage medium includes algorithm for identifying the optimal set of fluorophore-biomolecule reagent pairs by applying an iterative genetic algorithm.

BRIEF DESCRIPTION OF THE FIGURES

The patent or application the contains at least one drawing executed in color. Copies of this patent or patent application publication with color drawing(s) will be provided by the Office upon request and payment of the necessary fee.

The invention may be best understood from the following detailed description when read in conjunction with the accompanying drawings. Included in the drawings are the following figures.

DETAILED DESCRIPTION

Figure 1:
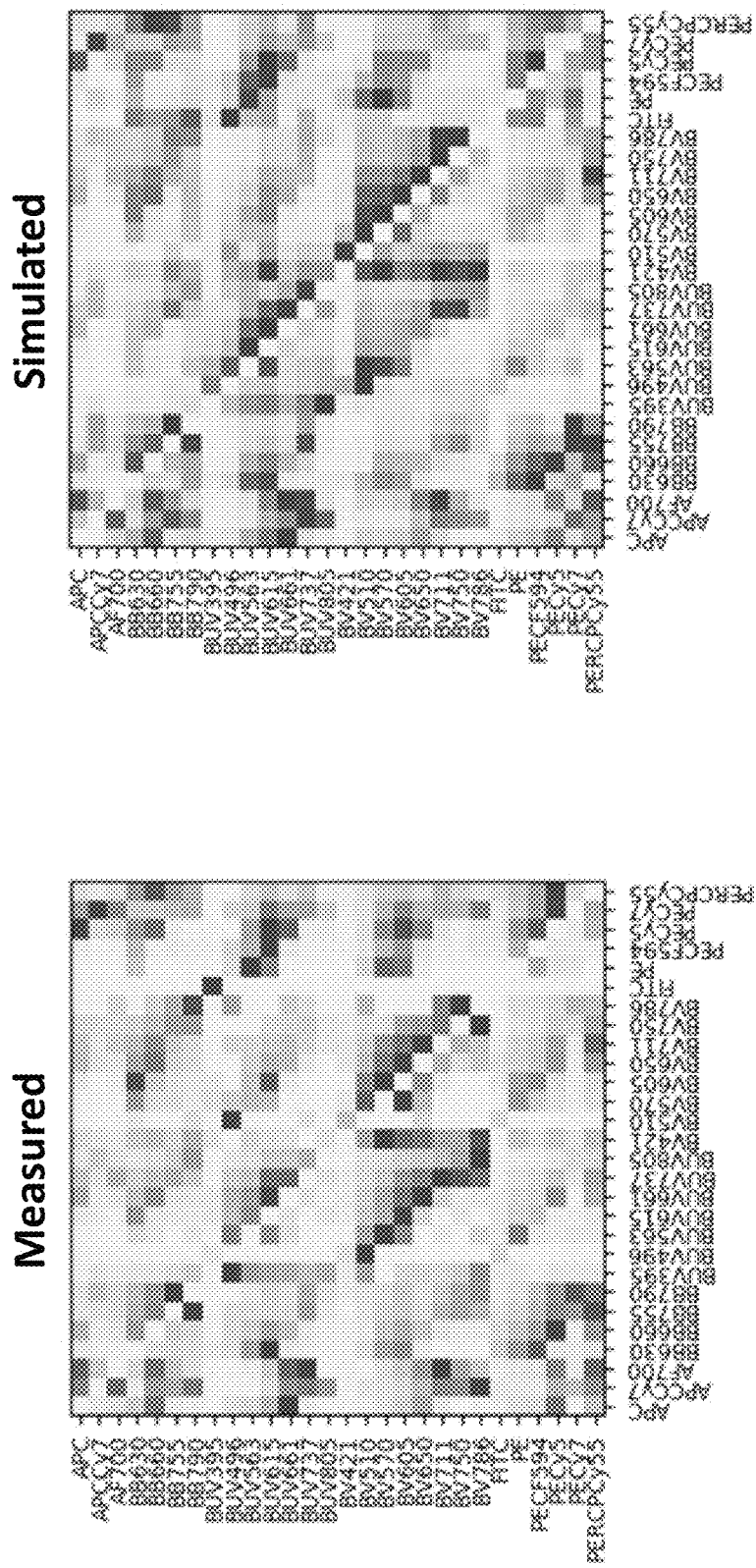
FIG. 1 depicts a comparison of measured spectral spillover spreading and simulated spectral spillover spreading between a set of fluorophores according to certain embodiments.

Aspects of the present disclosure include methods for identifying a set of fluorophore-biomolecule reagent pairs for characterizing a sample by flow cytometry. Methods according to certain embodiments include calculating a spectral spillover spreading parameter for a plurality of fluorophores, pairing each fluorophore with a biomolecule that is specific for a biomarker of a cell in the sample to generate a plurality of fluorophore-biomolecule reagent pairs, calculating an adjusted spillover spreading matrix for the fluorophore-biomolecule reagent pairs based on the spectral spillover spreading parameter of each fluorophore and a biomarker classification parameter and identifying an optimal set of fluorophore-biomolecule reagent pairs based on the calculated adjusted spillover spreading matrix. Systems and non-transitory computer readable storage medium for practicing the subject methods are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

As summarized above, the present disclosure provides methods for identifying a set of fluorophore-biomolecule reagent pairs for characterizing a sample by flow cytometry. In further describing embodiments of the disclosure, methods for identifying an optimal set of fluorophore-biomolecule reagent pairs based on a calculated adjusted spillover spreading matrix are first described in greater detail. Next, systems and non-transitory computer readable storage medium programmed to practice the subject methods, by calculating an adjusted spillover spreading matrix for a plurality of fluorophore-biomolecule reagent pairs are described.

Methods for Identifying a Set of Fluorophore-Biomolecule Reagent Pairs

Aspects of the present disclosure include methods for identifying a set of fluorophore-biomolecule reagent pairs for use in characterizing a sample, such as by flow cytometry. In embodiments, the subject methods provide for improved particle population resolution (e.g., identifying the population density of different type of cells in a sample with higher precision) by identifying an optimal set of fluorophore-biomolecule reagent pairs for characterizing the particles (e.g., cells) in a particular sample. In some embodiments, the subject methods provide for reduced spillover noise by fluorophores in the sample. In other embodiments, the subject methods provide for increased precision in quantifying molecular expression of biomarkers in a sample. The term "fluorophore-biomolecule reagent pair" refers to a biological macromolecule coupled (e.g., through a covalent bond) to a detectable fluorescent marker. The biological macromolecule may be a biopolymer. A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. Specifically, a "biopolymer" includes DNA (including cDNA), RNA and oligonucleotides, regardless of the source. As such, biomolecules may include polysaccharides, nucleic acids and polypeptides. For example, the nucleic acid may be an oligonucleotide, truncated or full-length DNA or RNA. In embodiments, oligonucleotides, truncated and full-length DNA or RNA are comprised of 10 nucleotide monomers or more, such as 15 or more, such as 25 or more, such as 50 or more, such as 100 or more, such as 250 or more and including 500 nucleotide monomers or more. For example, oligonucleotides, truncated and full-length DNA or RNA of interest may range in length from 10 nucleotides to $10^8$ nucleotides, such as from $10^2$ nucleotides to $10^7$ nucleotides, including from $10^3$ nucleotides to $10^6$ nucleotides. In embodiments, biopolymers are not single nucleotides or short chain oligonucleotides (e.g., less than 10 nucleotides). By "full length" is meant that the DNA or RNA is a nucleic acid polymer having 70% or more of its complete sequence (such as found in nature), such as 75% or more, such as 80% or more, such as 85% or more, such as 90% or more, such as 95% or more, such as 97% or more, such as 99% or more and including 100% of the full length sequence of the DNA or RNA (such as found in nature)

Polypeptides may be, in certain instances, truncated or full length proteins, enzyme or antibodies. In embodiments, polypeptides, truncated and full-length proteins, enzymes or antibodies are comprised of 10 amino acid monomers or more, such as 15 or more, such as 25 or more, such as 50 or more, such as 100 or more, such as 250 or more and including 500 amino acid monomers or more. For example, polypeptides, truncated and full-length proteins, enzymes or antibodies of interest may range in length from 10 amino acids to $10^8$ amino acids, such as from $10^2$ amino acids to $10^7$ amino acids, including from $10^3$ amino acids to $10^6$ amino acids. In embodiments, biopolymers are not single amino acids or short chain polypeptides (e.g., less than 10 amino acids). By "full length" is meant that the protein, enzyme or antibody is a polypeptide polymer having 70% or more of its complete sequence (such as found in nature), such as 75% or more, such as 80% or more, such as 85% or more, such as 90% or more, such as 95% or more, such as 97% or more, such as 99% or more and including 100% of the full length sequence of the protein, enzyme or antibody (such as found in nature). In certain embodiments, the biomolecule is an antibody.

In practicing the subject methods, a spectral spillover spreading parameter for a plurality of fluorophores is calculated. The term "spillover" is used herein in its conventional sense to refer to the partial overlap of emission spectra between two different fluorophores. In some instances, light spillover includes the light from fluorophores that have emission spectra which overlap with the detection ranges of non-target photodetectors. Depending on the number of fluorophore-biomolecule reagent pairs that are to be identified, the spectral spillover spreading parameter for 2 or more fluorophores may be calculated, such as 3 or more, such as 4 or more, such as 5 or more, such as 6 or more, such as 7 or more, such as 8 or more, such as 9 or more, such as 10 or more, such as 15 or more, such as 20 or more, such as 25 or more, such as 30 or more, such as 35 or more, such as 40 or more, such as 45 or more and including calculating spectral spillover spreading parameter for 50 or more fluorophores.

In embodiments, one or more of the fluorophores has a fluorescence spectrum that overlaps with the fluorescence spectrum of at least one other fluorophore in the plurality of fluorophores. In some instances, the overlap in fluorescence spectrum may be by 5 nm or more, such as by 10 nm or more, such as by 25 nm or more and including by 50 nm or more. In certain instances, the fluorescence spectra of one or more fluorophores in the plurality of fluorophores overlap with the fluorescence spectra of two or more different fluorophores in the sample, such as where each overlap in fluorescence spectra is by 5 nm or more, such as by 10 nm or more, such as by 25 nm or more and including by 50 nm or more. In other embodiments, the plurality of fluorophores have non-overlapping fluorescence spectra. In some embodiments, the fluorescence spectra of each fluorophore is adjacent to at least one other fluorophore within 10 nm or less, such as 9 nm or less, such as 8 nm or less, such as 7 nm or less, such as 6 nm or less, such as 5 nm or less, such as 4 nm or less, such as 3 nm or less, such as 2 nm or less and including 1 nm or less.

In some embodiments, methods for calculating the spectral spillover spreading parameter include detecting light from an irradiated sample having two or more fluorophores and measuring light intensity signals originating from a first fluorophore in the data signals obtained for one or more of the other fluorophores in the irradiated sample. In these embodiments, light emitted from a first fluorophore is collected by a detector that is configured to collect light emitted from one or more of the other fluorophores in the sample. In some embodiments, the spillover spreading parameter is the noise present in the light intensity data of a fluorophore that is caused by spillover light emission from one or more other fluorophores. In some embodiments, light from a first fluorophore adds intensity signal to a photodetector configured to detect light from one or more of the other fluorophores, i.e., the first fluorophore causes spillover into the light signals of the other fluorophores.

In some embodiments calculating the spectral spillover spreading parameter for each of the plurality of fluorophores includes quantifying the extent to which signal intensity data generated for a second fluorophore by a photodetector is impacted by the simultaneous collection of light from a first fluorophore by the same photodetector. In some instances, the spillover spreading parameter from one or more of the fluorophores is constructive (e.g., spillover spreading is impacted by signal intensities that are higher than would otherwise be observed). In other instances, the spillover spreading parameter from one or more of the fluorophores is destructive (e.g., spillover spreading is impacted by signal intensities that are lower than would otherwise be observed). In certain embodiments, calculating a spillover spreading parameter for each of the plurality of fluorophores includes a linear regression analysis. For example, the linear regression analysis may include calculating a linear fit between the zero-adjusted standard deviation and the median intensity of light collected for each fluorophore. In some embodiments, the zero-adjusted standard deviation is plotted along the y-axis and the median intensity of light collected from each fluorophore is plotted along the x-axis. The spillover spreading parameter may be determined from the slope of the linear fit calculated between the zero-adjusted standard deviation and the median intensity of light collected from each fluorophore. In some embodiments, the linear regression analysis is performed with an ordinary least squares regression model. In other embodiments, the linear regression analysis is performed with a weighted least squares model. In still other embodiments, the linear regression analysis is performed by a robust linear model.

In certain embodiments, the spillover spreading parameter for each fluorophore in the plurality of fluorophores may be calculated according to:

$$SS = \frac{\sqrt{\sigma^2 - \sigma_0^2}}{\sqrt{F}}$$

where SS is the calculated spillover spreading parameter of a first fluorophore; $\sigma$ is the standard deviation of light collected from a second, different fluorophore; $\sigma_0$ is the estimate of the standard deviation of the intensity of light collected from the second, different fluorophore based on the assumption that the intensity of light collected from the first fluorophore is zero; and F is the median intensity of light collected from the first fluorophore. In embodiments, a higher spillover spreading parameter corresponds to more spillover spreading for a given pair of first and second fluorophores.

In some embodiments, calculating a spectral spillover spreading parameter for the plurality of fluorophores includes calculating the spillover spreading for each possible combination of first and second fluorophores from the plurality of fluorophores. In some instances, the calculated spillover spreading for each possible combination of fluorophores is an approximation of the spectral spillover spread by each individual fluorophore into the other fluorophores. In certain embodiments, calculating the spectral spillover spreading parameter for each of the plurality of fluorophores includes generating a matrix of fluorescence spillover spreading values for the plurality of fluorophores where each fluorescence spillover spreading value in the matrix is calculated based on the fluorescence spillover spread of a fluorophore when in the presence of another fluorophore. Each column in the matrix corresponds to a detector configured to detect one of the plurality of different fluorophores, and each row in the matrix corresponds to a parameter of fluorophore that is detected. The cell in which a column and row intersects is populated with the calculated spillover spreading parameter value calculated for that pair of first and second fluorophore indicating the extent to which the fluorophore in question (i.e., the first fluorophore) contributes error to the relevant detector (i.e., detection of light emitted from the second fluorophore). In some embodiments, the fluorescence spillover spreading value is calculated based on the overlap of the fluorescence spectra of the two different fluorophores. In some instances, the total degree to which a fluorophore causes spillover spreading can be approximated by the values in its row in the generated matrix, and the total degree to which a detector is impacted by spillover spreading (by the other fluorophores) can be approximated by the values in its column in the generated matrix. In some embodiments, methods include calculating a sum of each row of the generated matrix. In certain instances, the sum of each row of the generated matrix is an approximation of the spectral spillover spread by each individual fluorophore into the plurality of fluorophores. In other embodiments, methods include calculating a sum of each column of the generated matrix. In certain instances, the sum of each column of the generated matrix is an approximation of the spectral spillover spread by the plurality of fluorophores into each individual fluorophore.

In certain embodiments, the spillover spreading parameters for each of the plurality of fluorophores (e.g., calculating each fluorophore fluorescence spillover spreading value in a generated spectral spillover spreading matrix) may be determined, such as described in Nguyen, et al. (Cytometry A 83(3): pp. 306-315 (2013) and U.S. Provisional Patent Application No. 63/020,758 filed on May 6, 2020 and U.S. Provisional Patent Application No. 63/076,611 filed on Sep. 10, 2020, the disclosures of which is herein incorporated by reference.

In some embodiments, calculating a spectral spillover parameter for each of the plurality of fluorophores includes simulating spectral properties of each fluorophore and calculating spillover spreading values for each of the fluorophores based on the simulated spectral properties. The term "simulate" is used herein in its conventional sense to refer to the computer modeling or generation of spectral data for each of the fluorophores by computational approximations. In embodiments, simulation of the spectral properties of each of the plurality of fluorophores may include simulation of one or more of the emission spectrum of the fluorophore, the excitation spectrum of the fluorophore, the quantum yield of the fluorophore and the extinction coefficient of the fluorophore. In some instances, calculating a spectral spillover parameter for each of the plurality of fluorophores by computer simulation includes computer modeling or computational approximation of system component responsivity, intensity and sensitivity, including but not limited to photodetectors, excitation lasers, optical relay components (e.g., fiber optics) and fixed sources of system component noise.

In some embodiments, methods include simulating spectral parameters of one or more of the plurality of fluorophores and generating a synthetic spectral spillover spreading matrix based on the simulated spectral parameters of the fluorophores. In these embodiments, the spectral spillover spreading parameters for each of the plurality of fluorophores may be calculated from the simulated spectral parameters using the generated synthetic matrix. In some embodiments, methods include calculating a sum of each row of the generated synthetic spectral spillover spreading matrix. In certain instances, the sum of each row of the generated synthetic spectral spillover spreading matrix is an approximation of the spectral spillover spread by each individual fluorophore into the plurality of fluorophores. In other embodiments, methods include calculating a sum of each column of the generated synthetic spectral spillover spreading matrix. In certain instances, the sum of each column of the generated synthetic spectral spillover spreading matrix is an approximation of the spectral spillover spread by the plurality of fluorophores into each individual fluorophore.

FIG. 1 depicts a comparison of measured spectral spillover spreading and simulated spectral spillover spreading between a set of 28 different fluorophores. The measured spillover spreading effect for each fluorophore pair is determined by irradiating a sample containing a first fluorophore and a second fluorophore and calculating the spectral spillover spreading effect of the first fluorophore on the second fluorophore and the spectral spillover spreading effect of the second fluorophore on the first fluorophore. The simulated spillover spreading effect is determined for each fluorophore pair based on the spectral properties of each of the plurality of fluorophores (emission spectra, excitation spectra, fluorophore quantum yield and fluorophore extinction coefficient) as well as based on one or more simulated system (e.g., flow cytometer) parameters (responsivity and sensitivity of photodetectors, optical relay components (e.g., fiber optics) and fixed sources of system component noise) In certain embodiments the generated matrix used in calculating a spectral spillover spreading parameter for each of the plurality of fluorophores includes a combination of measured spectral parameters and simulated spectral parameters. For example, the spectral parameters of one or more of the fluorophores in the matrix may be measured experimentally and the spectral parameters of one or more of the fluorophores in the matrix may be simulated. Depending on the number of fluorophores being characterized, the generated spectral spillover spreading matrix may include one or more experimentally determined fluorescence spillover spreading values, such as 2 or more, such as 3 or more, such as 4 or more, such as 5 or more, such as 6 or more, such as 7 or more, such as 8 or more, such as 9 or more, such as 10 or more, such as 15 or more, such as 20 or more and including 25 or more. In other instances, the generated spectral spillover spreading matrix may include one or more simulated fluorescence spillover spreading values, such as 2 or more, such as 3 or more, such as 4 or more, such as 5 or more, such as 6 or more, such as 7 or more, such as 8 or more, such as 9 or more, such as 10 or more, such as 15 or more, such as 20 or more and including 25 or more. In one example, 5% or more of the fluorescence spillover spreading values in the generated spectral spillover spreading matrix are simulated values, such as 10% or more, such as 20% or more, such as 30% or more, such as 40% or more, such as 50% or more, such as 60% or more, such as 70% or more, such as 80% or more, such as 90% or more and including where 95% or more of the fluorescence spillover spreading values in the generated spectral spillover spreading matrix are simulated values. In another example, 5% or more of the fluorescence spillover spreading values in the generated spectral spillover spreading matrix are experimentally determined values, such as 10% or more, such as 20% or more, such as 30% or more, such as 40% or more, such as 50% or more, such as 60% or more, such as 70% or more, such as 80% or more, such as 90% or more and including where 95% or more of the fluorescence spillover spreading values in the generated spectral spillover spreading matrix are experimentally determined values.

In embodiments, each fluorophore is paired with a biomolecule that is specific for a biomarker of a cell in the sample. In certain embodiments, the biomolecule is an antibody specific for one or more biomarkers on a biological cell, such as an immune cell. In some embodiments, the biomarker of interest is a cluster of differentiation protein biomarker (CD biomarker), such as a CD biomarker for stem cells (e.g., CD34+, CD31−, CD117), such as a CD biomarker for leukocyte groups (e.g., CD45+), such as a CD biomarker for granulocytes (e.g., CD45+, CD11 b, CD15+, CD24+, CD114+, CD182+), such as a CD biomarker for monocytes (e.g., CD4, CD45+, CD14+, CD114+, CD11a, CD11b, CD91+, CD16+), such as a CD biomarker for T lymphocytes (e.g., CD45+, CD3+), such as a CD biomarker for T helper cells (e.g., CD45+, CD3+, CD4+), such as a CD biomarker for T regulatory cells (e.g., CD4, CD25, FOXP3 (a transcription factor)), such as a CD biomarker for cytotoxic T cells (e.g., CD45+, CD3+, CD8+), such as a CD biomarker for B lymphocytes (e.g., CD45+, CD19+, CD20+, CD24+, CD38, CD22), such as a CD biomarker for thrombocytes (e.g., CD45+, CD61+), such as a CD biomarker for natural killer cells (e.g., CD16+, CD56+, CD3−, CD31, CD30, CD38). In certain embodiments, biomolecules of interest are specific for an antigen selected from one or more of CD3, CD4, CD8, CD16, CD27, CD45, CD56, CD69 and CD335.

Fluorophores of interest may include but are not limited to dyes, such as an acridine dye, anthraquinone dyes, arylmethane dyes, diarylmethane dyes (e.g., diphenyl methane dyes), chlorophyll containing dyes, triarylmethane dyes (e.g., triphenylmethane dyes), azo dyes, diazonium dyes, nitro dyes, nitroso dyes, phthalocyanine dyes, cyanine dyes, asymmetric cyanine dyes, quinon-imine dyes, azine dyes, eurhodin dyes, safranin dyes, indamins, indophenol dyes, fluorine dyes, oxazine dye, oxazone dyes, thiazine dyes, thiazole dyes, xanthene dyes, fluorene dyes, pyronin dyes, fluorine dyes, rhodamine dyes, phenanthridine dyes, as well as dyes combining two or more of the aforementioned dyes (e.g., in tandem), polymeric dyes having one or more monomeric dye units and mixtures of two or more of the aforementioned dyes thereof. A large number of dyes are commercially available from a variety of sources, such as, for example, Molecular Probes (Eugene, OR), Dyomics GmbH (Jena, Germany), Sigma-Aldrich (St. Louis, MO), Sirigen, Inc. (Santa Barbara, CA) and Exciton (Dayton, OH). For example, the fluorophore may include 4-acetamido-4'-isothiocyanatostilbene-2,2'disulfonic acid; acridine and derivatives such as acridine, acridine orange, acridine yellow, acridine red, and acridine isothiocyanate; allophycocyanin, phycoerythrin, peridinin-chlorophyll protein, 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy3.5, Cy5, Cy5.5, and Cy7; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; dye-conjugated polymers (i.e., polymer-attached dyes) such as fluorescein isothiocyanate-dextran as well as dyes combining two or more dyes (e.g., in tandem), polymeric dyes having one or more monomeric dye units and mixtures of two or more of the aforementioned dyes or combinations thereof.

In some instances, the fluorophore is polymeric dye. Polymeric dyes of interest include, but are not limited to, those dyes described by Gaylord et al. in U.S. Publication Nos. 20040142344, 20080293164, 20080064042, 20100136702, 20110256549, 20110257374, 20120028828, 20120252986, 20130190193, 20160264737, 20160266131, 20180231530, 20180009990, 20180009989, and 20180163054, the disclosures of which are herein incorporated by reference in their entirety; and Gaylord et al., J. Am. Chem. Soc., 2001, 123 (26), pp 6417-6418; Feng et al., Chem. Soc. Rev., 2010, 39, 2411-2419; and Traina et al., J. Am. Chem. Soc., 2011, 133 (32), pp 12600-12607, the disclosures of which are herein incorporated by reference in their entirety. The polymeric dye may have one or more desirable spectroscopic properties, such as a particular absorption maximum wavelength, a particular emission maximum wavelength, extinction coefficient, quantum yield, and the like (see e.g., Chattopadhyay et al., "Brilliant violet fluorophores: A new class of ultrabright fluorescent compounds for immunofluorescence experiments." Cytometry Part A, 81A(6), 456-466, 2012). In some embodiments, the polymeric dye has an absorption curve between 280 nm and 475 nm. In certain embodiments, the polymeric dye has an absorption maximum (excitation maximum) in the range 280 nm and 475 nm. In some embodiments, the polymeric dye absorbs incident light having a wavelength in the range between 280 nm and 475 nm. In some embodiments, the polymeric dye has an emission maximum wavelength ranging from 400 nm to 850 nm, such as 415 nm to 800 nm, where specific examples of emission maxima of interest include, but are not limited to: 421 nm, 510 nm, 570 nm, 602 nm, 650 nm, 711 nm and 786 nm. In some instances, the polymeric dye has an emission maximum wavelength in a range selected from the group consisting of 410 nm to 430 nm, 500 nm to 520 nm, 560 nm to 580 nm, 590 nm to 610 nm, 640 nm to 660 nm, 700 nm to 720 nm, and 775 nm to 795 nm. In certain embodiments, the polymeric dye has an emission maximum wavelength of 421 nm. In some instances, the polymeric dye has an emission maximum wavelength of 510 nm. In some cases, the polymeric dye has an emission maximum wavelength of 570 nm. In certain embodiments, the polymeric dye has an emission maximum wavelength of 602 nm. In some instances, the polymeric dye has an emission maximum wavelength of 650 nm. In certain cases, the polymeric dye has an emission maximum wavelength of 711 nm. In some embodiments, the polymeric dye has an emission maximum wavelength of 786 nm. In certain instances, the polymeric dye has an emission maximum wavelength of 421 nm±5 nm. In some embodiments, the polymeric dye has an emission maximum wavelength of 510 nm±5 nm. In certain instances, the polymeric dye has an emission maximum wavelength of 570 nm±5 nm. In some instances, the polymeric dye has an emission maximum wavelength of 602 nm±5 nm. In some embodiments, the polymeric dye has an emission maximum wavelength of 650 nm±5 nm. In certain instances, the polymeric dye has an emission maximum wavelength of 711 nm±5 nm. In some cases, the polymeric dye has an emission maximum wavelength of 786 nm±5 nm. In certain embodiments, the polymeric dye has an emission maximum selected from the group consisting of 421 nm, 510 nm, 570 nm, 602 nm, 650 nm, 711 nm and 786 nm. Specific polymeric dyes that may be employed include, but are not limited to, BD Horizon Brilliant™ Dyes, such as BD Horizon Brilliant™ Violet Dyes (e.g., BV421, BV510, BV605, BV650, BV711, BV786); BD Horizon Brilliant™ Ultraviolet Dyes (e.g., BUV395, BUV496, BUV737, BUV805); and BD Horizon Brilliant™ Blue Dyes (e.g., BB515).

In embodiments for identifying an optimal set of fluorophore-biomolecule reagent pairs according to the subject methods, each fluorophore is paired with biomolecules to generate a plurality of different fluorophore-biomolecule reagent pairs. In some embodiments, each biomolecule is paired with 1 or more different fluorophores, such as 2 or more different fluorophores, such as 3 or more different fluorophores, such as 4 or more different fluorophores, such as 5 or more different fluorophores, such as 6 or more different fluorophores, such as 7 or more different fluorophores, such as 8 or more different fluorophores, such as 9 or more different fluorophores, such as 10 or more different fluorophores, such as 15 or more different fluorophores, such as 20 or more different fluorophores, such as 25 or more different fluorophores, such as 30 or more different fluorophores, such as 35 or more different fluorophores, such 40 or more different fluorophores, such as 45 or more different fluorophores and including pairing each biomolecule with 45 or more different fluorophores to generate the plurality of different fluorophore-biomolecule reagent pairs.

In embodiments, methods include generating an adjusted spillover spreading matrix for the fluorophore-biomolecule reagent pairs based on the spectral spillover spreading parameter (measured or simulated) of each fluorophore and a biomarker classification parameter. In some embodiments, the biomarker classification parameter includes a quantitative population density component for each biomarker in the sample. In some instances, the quantitative population density is a numerical range of the population of each biomarker in the sample. In other instances, the biomarker classification parameter is a semi-quantitative population density classification for each biomarker in the sample. For example, the semi-quantitative population density classification may be a designation of biomarker expression, such as where the designation of biomarker expression is 1) very high biomarker expression; 2) high biomarker expression; 3) medium biomarker expression; 4) low biomarker expression and 5) absent biomarker expression. In yet other instances, the biomarker classification parameter includes a qualitative population density classification for each biomarker in the sample. In certain instances, the qualitative population density classification for each biomarker in the sample is a binary biomarker classification. In one example, the binary biomarker classification may be a designation according to whether a biomarker is present or absent. In another example, the binary biomarker classification may be a designation according to whether a biomarker is expected to be present in the sample above a predetermined threshold (e.g., a minimum antigen density). In yet another example, the binary biomarker classification may be a designation of the criticality of the biomarker to an identified set of fluorophore-biomolecule reagent pairs. For instance, the binary biomarker classification may be a designation of a biomarker as being 1) critical or 2) non-critical to the identified set of fluorophore-biomolecule reagent pairs.

In certain embodiments, an adjusted spillover spreading matrix is generated by calculating an adjusted spillover spreading parameter value (SS value, described above) of a fluorophore based on a population density value of a biomarker. In some instances, the adjusted SS values describe the amount of excess spillover spreading in the measured value of a first fluorophore (i.e., "receiving" fluorophore) due to fluorescence of a second, different fluorophore (i.e., a spillover "source" fluorophore). In certain instances, the standard deviation of the first fluorophore increases proportionally to the square root of the expression level of the second fluorophore.

In some embodiments, calculating an adjusted spillover spreading parameter based on a population density value of a biomarker includes: (1) multiplying the spillover spreading parameter value (SS value) by the square root of the population density value of the biomarker of the second fluorophore to generate a standard deviation in expression of the first fluorophore, and (2) dividing the adjusted spillover spreading parameter value (SS value) by the population density value of a biomarker of the first fluorophore to generate a count value (CV). In some instances, the count value describes spillover spread in the first fluorophore relative to expression level of the first fluorophore.

In certain embodiments, methods include calculating a total spillover spreading parameter into a fluorophore from a plurality of fluorophores based on population density values of a plurality of biomarkers. In some instances, a matrix of the spillover spreading parameter values is generated where each row of the matrix corresponds to a first fluorophore (e.g., a spillover source fluorophore) and each column corresponds to a second fluorophore (e.g., a spillover receiving fluorophore), so that the values in the matrix (e.g., entry in row i and column j) correspond to an increased standard deviation in expression of the first fluorophore (e.g., fluorophore j) per square root unit of expression of the second fluorophore (e.g. fluorophore i). In certain instances, the total spillover spreading parameter of the fluorophore from the plurality of fluorophores is determined by: 1) calculating the sum of squared adjusted spillover spreading parameter values for each fluorophore; 2) determining the square root of the sum of squared adjusted spillover spreading parameter values to generate a standard deviation or CV of the fluorophore.

In certain embodiments, methods include calculating a total spillover spreading parameter of a fluorophore from a generated spillover spreading matrix by: calculating a sum of squared adjusted spillover spreading values in a column corresponding to a second fluorophore and determining a square root of the sum of squared adjusted spillover spreading values in the column. In certain instances, a total spillover spreading parameter of a fluorophore is calculated from a generated spillover spreading matrix according to:

$$ColSum = \frac{1}{AgDens_{col}} \left( \sum_{row=1}^{N_{rows}} AgDens_{row}(SS_{col}^{row})^2 \right)^{1/2}$$

In practicing the subject methods, the calculated adjusted spillover spreading matrix for the plurality of fluorophore-biomolecule reagent pairs is used to identify an optimal set of fluorophore-biomolecule reagent pairs for characterizing the sample by flow cytometry. In some embodiments, identifying the optimal set of fluorophore-biomolecule reagent pairs includes a reagent pair ranking algorithm, such as where each of the fluorophore-biomolecule reagent pairs is assigned a score based on the calculated adjusted spillover spreading matrix value for each fluorophore-biomolecule reagent pair. In some embodiments, identifying the optimal set of fluorophore-biomolecule reagent pairs includes selecting the fluorophore-biomolecule reagent pairs having the lowest score based on the calculated adjusted spillover spreading matrix. In other embodiments, identifying the optimal set of fluorophore-biomolecule reagent pairs includes selecting the fluorophore-biomolecule reagent pairs having a score that is below a predetermined threshold based on the calculated adjusted spillover spreading matrix. In yet other embodiments, identifying the optimal set of fluorophore-biomolecule reagent pairs includes selecting at random a predetermined number of the fluorophore-biomolecule reagent pairs. In other embodiments, identifying the optimal set of fluorophore-biomolecule reagent pairs includes applying a constrained optimization algorithm, such as where each fluorophore-biomolecule reagent pair is selected at random and subjected to a set of constraints to generate a constrained set of fluorophore-biomolecule reagent pairs. In certain embodiments, the constrained optimization algorithm includes solving a constrained optimization problem (COP). In other embodiments, the constrained optimization algorithm includes solving a constrained satisfaction problem (CSP). In certain instances, the constrained optimization algorithm includes a constraint satisfaction algorithm in which fluorophore-biomolecule reagent pairs are selected to satisfy a predetermined constraint such that each fluorophore-biomolecule reagent pair does not cause excess spillover spreading into other fluorophore-biomolecule reagent pairs in a predetermined subpopulation.

In certain embodiments, identifying the optimal set of fluorophore-biomolecule reagent pairs includes applying an iterative genetic algorithm to identify an optimal set of fluorophore-biomolecule reagent pairs. The term "genetic algorithm" is used herein in its conventional sense to refer to an algorithm for solving constrained or unconstrained optimization problems by iteration toward better, higher quality solutions and may include operators such as mutation, crossover and selection of preferred solutions. Each step for iteratively selecting an optimal set of fluorophore-biomolecule reagent pairs may be repeated one or more times, such as 2 or more times, such as 3 or more times, such as 4 or more times, such as 5 or more times, such as 10 or more times, such as 15 or more times, such as 25 or more times, such as 50 or more times and including 100 or more times, as desired.

In certain embodiments, identifying a set of fluorophore-biomolecule reagent pairs for characterizing a sample by flow cytometry according to the subject methods is performed in the absence of data collection from an experimental sample (e.g., a sample having fluorophores being irradiated by a light source). For example, one or more steps of the subject methods described herein may be simulated or data may be retrieved from a database (e.g., a local database stored on computer readable storage media, a local data server or from a remote location such as a cloud-based data server). In certain instances, calculations according to the subject methods are performed in the absence of any experimentally measured values. In practicing the subject methods, a population of different fluorophore-biomolecule reagent pairs is identified. In some embodiments, methods further include mutating one or more of the fluorophore-biomolecule reagent pairs in the identified population to produce a mutated population of fluorophore-biomolecule reagent pairs. In other embodiments, methods include mating two or more different fluorophore-biomolecule reagent pairs from the identified population and the mutated population to produce an offspring population of fluorophore-biomolecule reagent pairs, where each offspring fluorophore-biomolecule reagent pairs includes fluorophore parameters and biomolecule parameters randomly selected from the mated fluorophore-biomolecule reagent pairs. The term "mating" is used herein in its conventional sense to refer to combining two or more of the different fluorophore-biomolecule reagent pairs of the identified population and the mutated population such that the offspring population of fluorophore-biomolecule reagent pairs has characteristics of the parent population (i.e., identified population or mutated population). Any number of fluorophore-biomolecule reagent pairs may be mated from the identified population of fluorophore-biomolecule reagent pairs and mutated population of fluorophore-biomolecule reagent pairs, such as 3 or more, such as 4 or more, such as 5 or more, such as 6 or more, such as 8 or more, such as 10 or more and including 20 or more. In these embodiments, any combination of different fluorophore-biomolecule reagent pairs from each population (e.g., identified population, mutated population) may be combined, such as where one or more fluorophore-biomolecule reagent pairs from the identified population is mated with one or more of the fluorophore-biomolecule reagent pairs of the mutated population. In some embodiments, methods may include repeating one or more steps of each optimization interval (i.e., mutating, mating, ranking) until an optimal set of fluorophore-biomolecule reagent pairs have been determined, such as repeating each optimization step N times, where N is 2 or more, such as 3 or more, such as 4 or more, such as 5 or more, such as 10 or more, such as 15 or more, such as 20 or more, such as 25 or more, such as 50 or more, such as 75 or more, such as 100 or more and including where N is 250 or more.

Figure 2:
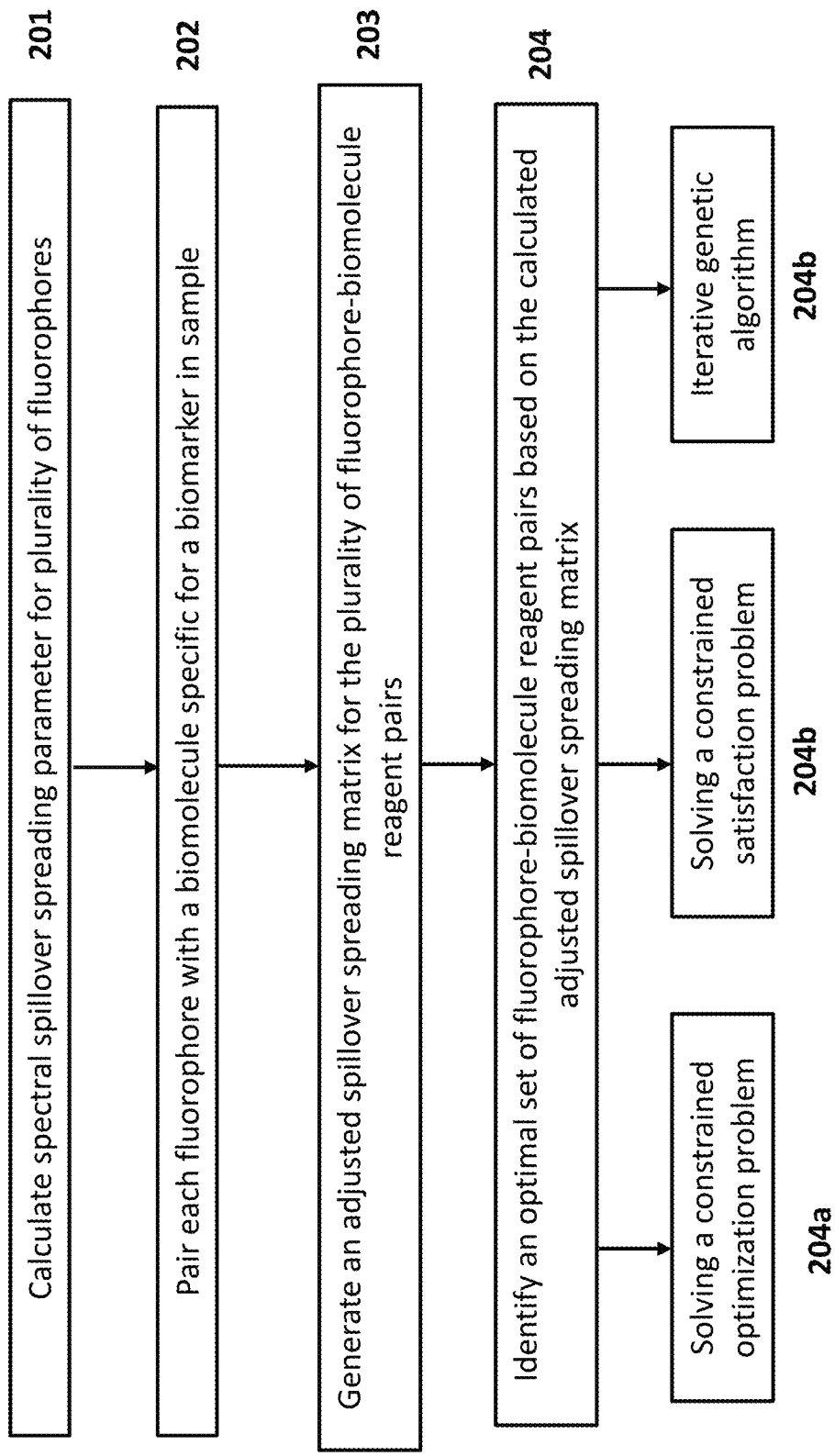
FIG. 2 depicts a flow chart for identifying a set of fluorophore-biomolecule reagent pairs according to certain embodiments.

FIG. 2 depicts a flow chart for identifying a set of fluorophore-biomolecule reagent pairs according to certain embodiments. At step 201, a spectral spillover parameter for a plurality of fluorophores is calculated. In certain instances, calculating spectral spillover parameters for each of the fluorophores includes generating a matrix of fluorescence spillover spreading values for the plurality of fluorophores where each fluorescence spillover spreading value in the matrix is calculated based on the fluorescence spillover spread of a fluorophore when in the presence of another fluorophore of the plurality of fluorophores. Each fluorophore at step 202 is paired with a biomolecule that is specific for a biomarker of a cell (e.g., an antibody specific for a CD biomarker of human immune cells) to generate a plurality of different fluorophore-biomolecule reagent pairs. At step 203, an adjusted spillover spreading matrix for the fluorophore-biomolecule reagent pairs is generated based on the spectral spillover spreading parameter of each fluorophore and a biomarker classification parameter for each of the biomarkers specific to the paired biomolecules. In some instances, the biomarker classification is a quantitative classification, such as an antigen population density numerical range. In other instances, the biomarker classification is a semi-quantitative classification, such as a semi-quantitative designation of biomarker expression (e.g., very high biomarker expression). In other instances, the biomarker classification is a binary classification, such as a designation of the presence or absence of biomarker expression. Based on the adjusted spillover spreading matrix, an optimal set of fluorophore-biomolecule reagent pairs are identified at step 204. In some instances, the optimal set of fluorophore-biomolecule reagent pairs is identified using a constrained optimization algorithm, such as solving a constrained optimization problem (204*a*) or solving a constrained satisfaction problem (204*b*). In certain instances, optimal set of fluorophore-biomolecule reagent pairs is identified by applying an iterative genetic algorithm (204*c*).

In certain embodiments, methods further include characterizing a sample having cells by flow cytometry with the identified optimal set of fluorophore-biomolecule reagent pairs. In some embodiments, the sample is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

In some embodiments, a sample (e.g., in a flow stream of the flow cytometer) is irradiated with light from a light source. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Where methods include irradiating with a broadband light source, broadband light source protocols of interest may include, but are not limited to, a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, methods includes irradiating with a narrow band light source emitting a particular wavelength or a narrow range of wavelengths, such as for example with a light source which emits light in a narrow range of wavelengths like a range of 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Where methods include irradiating with a narrow band light source, narrow band light source protocols of interest may include, but are not limited to, a narrow wavelength LED, laser diode or a broadband light source coupled to one or more optical bandpass filters, diffraction gratings, monochromators or any combination thereof.

In certain embodiments, methods include irradiating the sample with one or more lasers. As discussed above, the type and number of lasers will vary depending on the sample as well as desired light collected and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the methods include irradiating the flow stream with a dye laser, such as a stilbene, coumarin or rhodamine laser. In yet other instances, methods include irradiating the flow stream with a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, methods include irradiating the flow stream with a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulium YAG laser, ytterbium YAG laser, ytterbium$_2$O$_3$ laser or cerium doped lasers and combinations thereof.

The sample may be irradiated with one or more of the above mentioned light sources, such as 2 or more light sources, such as 3 or more light sources, such as 4 or more light sources, such as 5 or more light sources and including 10 or more light sources. The light source may include any combination of types of light sources. For example, in some embodiments, the methods include irradiating the sample in the flow stream with an array of lasers, such as an array having one or more gas lasers, one or more dye lasers and one or more solid-state lasers.

In certain instances, the flow stream is irradiated with a plurality of beams of frequency-shifted light and a cell in the flow stream is imaged by fluorescence imaging using radiofrequency tagged emission (FIRE) to generate a frequency-encoded image, such as those described in Diebold, et al. Nature Photonics Vol. 7(10); 806-810 (2013) as well as described in U.S. Pat. Nos. 9,423,353; 9,784,661 and 10,006,852 and U.S. Patent Publication Nos. 2017/0133857 and 2017/0350803, the disclosures of which are herein incorporated by reference.

Aspects of the present invention include collecting fluorescent light with a fluorescent light detector. A fluorescent light detector may, in some instances, be configured to detect fluorescence emissions from fluorescent molecules, e.g., labeled specific binding members (such as labeled antibodies that specifically bind to markers of interest) associated with the particle in the flow cell. In certain embodiments, methods include detecting fluorescence from the sample with one or more fluorescent light detectors, such as 2 or more, such as 3 or more, such as 4 or more, such as 5 or more, such as 6 or more, such as 7 or more, such as 8 or more, such as 9 or more, such as 10 or more, such as 15 or more and including 25 or more fluorescent light detectors. In embodiments, each of the fluorescent light detectors is configured to generate a fluorescence data signal. Fluorescence from the sample may be detected by each fluorescent light detector, independently, over one or more of the wavelength ranges of 200 nm-1200 nm. In some instances, methods include detecting fluorescence from the sample over a range of wavelengths, such as from 200 nm to 1200 nm, such as from 300 nm to 1100 nm, such as from 400 nm to 1000 nm, such as from 500 nm to 900 nm and including from 600 nm to 800 nm. In other instances, methods include detecting fluorescence with each fluorescence detector at one or more specific wavelengths. For example, the fluorescence may be detected at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof, depending on the number of different fluorescent light detectors in the subject light detection system. In certain embodiments, methods include detecting wavelengths of light which correspond to the fluorescence peak wavelength of certain fluorophores present in the sample. In embodiments, fluorescent flow cytometer data is received from one or more fluorescent light detectors (e.g., one or more detection channels), such as 2 or more, such as 3 or more, such as 4 or more, such as 5 or more, such as 6 or more and including 8 or more fluorescent light detectors (e.g., 8 or more detection channels).

Light from the sample may be measured at one or more wavelengths of, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring the collected light at 400 or more different wavelengths.

In certain embodiments, methods include spectrally resolving the light from each fluorophore of the fluorophore-biomolecule reagent pairs in the sample. In some embodiments, the overlap between each different fluorophore is determined and the contribution of each fluorophore to the overlapping fluorescence is calculated. In some embodiments, spectrally resolving light from each fluorophore includes calculating a spectral unmixing matrix for the fluorescence spectra for each of the plurality of fluorophores having overlapping fluorescence in the sample detected by the light detection system. In certain instances, spectrally resolving the light from each fluorophore and calculating a spectral unmixing matrix for each fluorophore may be used to estimate the abundance of each fluorophore, such as for example to resolve the abundance of target cells in the sample.

In certain embodiments, methods include spectrally resolving light detected by a plurality of photodetectors such as described e.g., in International Patent Application No. PCT/US2019/068395 filed on Dec. 23, 2019; U.S. Provisional Patent Application No. 62/971,840 filed on Feb. 7, 2020 and U.S. Provisional Patent Application No. 63/010,890 filed on Apr. 16, 2020, the disclosures of which are herein incorporated by reference in their entirety. For example, spectrally resolving light detected by the plurality of photodetectors of the second set of photodetectors may be include solving a spectral unmixing matrix using one or more of: 1) a weighted least square algorithm; 2) a Sherman-Morrison iterative inverse updater; 3) an LU matrix decomposition, such as where a matrix is decomposed into a product of a lower-triangular (L) matrix and an upper-triangular (U) matrix; 4) a modified Cholesky decomposition; 5) by QR factorization; and 6) calculating a weighted least squares algorithm by singular value decomposition.

In certain embodiments, methods further include characterizing the spillover spreading of the light detected by a plurality of photodetectors such as described e.g., in U.S. Provisional Patent Application No. 63/020,758 filed on May 6, 2020 and U.S. Provisional Patent Application No. 63/076,611 filed on Sep. 10, 2020, the disclosures of which are herein incorporated by reference.

In certain instances, the abundance of fluorophores associated with (e.g., chemically associated (i.e., covalently, ionically) or physically associated) a target particle is calculated from the spectrally resolved light from each fluorophore associated with the particle. For instance, in one example the relative abundance of each fluorophore associated with a target particle is calculated from the spectrally resolved light from each fluorophore. In another example, the absolute abundance of each fluorophore associated with the target particle is calculated from the spectrally resolved light from each fluorophore. In certain embodiments, a particle may be identified or classified based on the relative abundance of each fluorophore determined to be associated with the particle. In these embodiments, the particle may be identified or classified by any convenient protocol such as by: comparing the relative or absolute abundance of each fluorophore associated with a particle with a control sample having particles of known identity; or by conducting spectroscopic or other assay analysis of a population of particles (e.g., cells) having the calculated relative or absolute abundance of associated fluorophores.

In certain embodiments, methods include sorting one or more of the particles (e.g., cells) of the sample that are identified based on the estimated abundance of the fluorophores associated with the particle. The term "sorting" is used herein in its conventional sense to refer to separating components (e.g., droplets containing cells, droplets containing non-cellular particles such as biological macromolecules) of a sample and in some instances, delivering the separated components to one or more sample collection containers. For example, methods may include sorting 2 or more components of the sample, such as 3 or more components, such as 4 or more components, such as 5 or more components, such as 10 or more components, such as 15 or more components and including sorting 25 or more components of the sample.

In sorting particles identified based on the abundance of fluorophores associated with the particle, methods include data acquisition, analysis and recording, such as with a computer, where multiple data channels record data from each detector used in obtaining the overlapping spectra of the plurality of fluorophore-biomolecule reagent pairs associated with the particle. In these embodiments, analysis includes spectrally resolving light (e.g., by calculating the spectral unmixing matrix) from the plurality of fluorophores of the fluorophore-biomolecule reagent pairs having overlapping spectra that are associated with the particle and identifying the particle based on the estimated abundance of each fluorophore associated with the particle. This analysis may be conveyed to a sorting system which is configured to generate a set of digitized parameters based on the particle classification.

In some embodiments, methods for sorting components of a sample include sorting particles (e.g., cells in a biological sample), such as described in U.S. Pat. Nos. 3,960,449; 4,347,935; 4,667,830; 5,245,318; 5,464,581; 5,483,469; 5,602,039; 5,643,796; 5,700,692; 6,372,506 and 6,809,804, the disclosures of which are herein incorporated by reference. In some embodiments, methods include sorting components of the sample with a particle sorting module, such as those described in U.S. Pat. Nos. 9,551,643 and 10,324,019, U.S. Patent Publication No. 2017/0299493 and International Patent Publication No. WO/2017/040151, the disclosure of which is incorporated herein by reference. In certain embodiments, cells of the sample are sorted using a sort decision module having a plurality of sort decision units, such as those described in U.S. patent application Ser. No. 16/725,756, filed on Dec. 23, 2019, the disclosure of which is incorporated herein by reference.

Systems for Identifying a Set of Fluorophore-Biomolecule Reagent Pairs

As summarized above, aspects of the present disclosure also include systems for identifying a set of fluorophore-biomolecule reagent pairs for characterizing a sample, such as a sample having a population of cells. Systems according to certain embodiments include a processor having memory operably coupled to the processor where the memory includes instructions stored thereon, which when executed by the processor, cause the processor to: calculate a spectral spillover spreading parameter for a plurality of fluorophores, pair each fluorophore with a biomolecule that is specific for a biomarker of a cell in the sample to generate a plurality of fluorophore-biomolecule reagent pairs, generate an adjusted spillover spreading matrix for the fluorophore-biomolecule reagent pairs based on the spectral spillover spreading parameter of each fluorophore and a biomarker classification parameter and identify an optimal set of fluorophore-biomolecule reagent pairs based on the calculated spillover spreading values from the adjusted spillover spreading matrix.

In embodiments, systems include memory having instructions stored thereon, which when executed by the processor, cause the processor to calculate a spectral spillover spreading parameter for a plurality of fluorophores. Depending on the desired number of fluorophore-biomolecule reagent pairs in the identified panel of fluorophore-biomolecule reagent pairs, the memory may include instructions for calculating a spectral spillover spreading parameter for 2 or more fluorophores, such as 3 or more, such as 4 or more, such as 5 or more, such as 6 or more, such as 7 or more, such as 8 or more, such as 9 or more, such as 10 or more, such as 15 or more, such as 20 or more, such as 25 or more, such as 30 or more, such as 35 or more, such as 40 or more, such as 45 or more and including instructions for calculating spectral spillover spreading parameter for 50 or more fluorophores.

In embodiments, one or more of the fluorophores has a fluorescence spectrum that overlaps with the fluorescence spectrum of at least one other fluorophore in the plurality of fluorophores. In some instances, the overlap in fluorescence spectrum may be by 5 nm or more, such as by 10 nm or more, such as by 25 nm or more and including by 50 nm or more. In certain instances, the fluorescence spectra of one or more fluorophores in the plurality of fluorophores overlap with the fluorescence spectra of two or more different fluorophores in the sample, such as where each overlap in fluorescence spectra is by 5 nm or more, such as by 10 nm or more, such as by 25 nm or more and including by 50 nm or more. In other embodiments, the plurality of fluorophores have non-overlapping fluorescence spectra. In some embodiments, the fluorescence spectra of each fluorophore is adjacent to at least one other fluorophore within 10 nm or less, such as 9 nm or less, such as 8 nm or less, such as 7 nm or less, such as 6 nm or less, such as 5 nm or less, such as 4 nm or less, such as 3 nm or less, such as 2 nm or less and including 1 nm or less.

In some embodiments, the memory includes instructions for calculating the spectral spillover spreading parameter by detecting light from an irradiated sample having two or more fluorophores and measuring light intensity signals originating from a first fluorophore in the data signals obtained for one or more of the other fluorophores in the irradiated sample. In some instances, the memory includes instructions for calculating the spectral spillover spreading parameter for each of the plurality of fluorophores by quantifying the extent to which signal intensity data generated for a second fluorophore by a photodetector is impacted by the simultaneous collection of light from a first fluorophore by the same photodetector. In some instances, the spillover spreading parameter from one or more of the fluorophores is constructive (e.g., spillover spreading is impacted by signal intensities that are higher than would otherwise be observed). In other instances, the spillover spreading parameter from one or more of the fluorophores is destructive (e.g., spillover spreading is impacted by signal intensities that are lower than would otherwise be observed).

In certain embodiments, the memory includes instructions for calculating a spillover spreading parameter for each of the plurality of fluorophores by a linear regression analysis. For example, the memory may include instructions for performing a linear regression analysis that includes calculating a linear fit between the zero-adjusted standard deviation and the median intensity of light collected for each fluorophore. In some embodiments, the memory includes instructions stored thereon for plotting the zero-adjusted standard deviation along the y-axis and plotting the median intensity of light collected from each fluorophore along the x-axis. In these embodiments, the memory may include instructions for determining the spillover spreading parameter from the slope of the linear fit calculated between the zero-adjusted standard deviation and the median intensity of light collected from each fluorophore. In some embodiments, the memory includes instructions for performing the linear regression analysis with an ordinary least squares regression model. In other embodiments, the memory includes instructions for performing the linear regression analysis with a weighted least squares model. In still other embodiments, the memory includes instructions for performing the linear regression analysis by a robust linear model.

In certain instances, the memory includes instructions for calculating the spillover spreading parameter for each fluorophore in the plurality of fluorophores according to:

$$SS = \frac{\sqrt{\sigma^2 - \sigma_0^2}}{\sqrt{F}}$$

where SS is the calculated spillover spreading parameter of a first fluorophore; $\sigma$ is the standard deviation of light collected from a second, different fluorophore; $\sigma_0$ is the estimate of the standard deviation of the intensity of light collected from the second, different fluorophore based on the assumption that the intensity of light collected from the first fluorophore is zero; and F is the median intensity of light collected from the first fluorophore. In embodiments, a higher spillover spreading parameter corresponds to more spillover spreading for a given pair of first and second fluorophores.

In some embodiments, the memory includes instructions for calculating a spectral spillover spreading parameter for the plurality of fluorophores by calculating the spillover spreading for each possible combination of first and second fluorophores in the plurality of fluorophores. In some instances, the calculated spillover spreading for each possible combination of fluorophores is an approximation of the spectral spillover spread by each individual fluorophore into the other fluorophores of the plurality of fluorophores. In certain embodiments, the memory includes instructions for calculating the spectral spillover spreading parameter for each of the plurality of fluorophores by generating a matrix of fluorescence spillover spreading values for the plurality of fluorophores. In these embodiments, the memory includes instructions for calculating each fluorescence spillover spreading value in the matrix based on the fluorescence spillover spread of a fluorophore when in the presence of another fluorophore of the plurality of fluorophores. Each column in the matrix corresponds to a detector configured to detect one of the plurality of different fluorophores, and each row in the matrix corresponds to a parameter of fluorophore that is detected. The cell in which a column and row intersects is populated with the calculated spillover spreading parameter value calculated for that pair of first and second fluorophore indicating the extent to which the fluorophore in question (i.e., the first fluorophore) contributes error to the relevant detector (i.e., detection of light emitted from the second fluorophore). In some embodiments, the memory includes instructions for calculating the fluorescence spillover spreading value based on the overlap of the fluorescence spectra of the two different fluorophores. In some instances, the memory includes instructions for approximating the total degree to which a fluorophore causes spillover spreading based on the values in its row of the generated matrix, and instructions for approximating the total degree to which a detector is impacted by spillover spreading (by the other fluorophores) based on the values in its column in the generated matrix. In some embodiments, the memory includes instructions for calculating a sum of each row of the generated matrix. In certain instances, the sum of each row of the generated matrix is an approximation of the spectral spillover spread by each individual fluorophore into the plurality of fluorophores. In other embodiments, the memory includes instructions for calculating a sum of each column of the generated matrix. In certain instances, the sum of each column of the generated matrix is an approximation of the spectral spillover spread by the plurality of fluorophores into each individual fluorophore.

In certain embodiments, systems of interest include memory having instructions stored thereon, which when executed by a processor, cause the processor to simulate a spectral spillover parameter for each of the plurality of fluorophores. In these embodiments, the memory may include instructions for simulating spectral properties of each fluorophore and calculating spillover spreading values for each of the fluorophores based on the simulated spectral properties. In some embodiments, simulation of the spectral properties of each of the plurality of fluorophores by the subject systems may include simulation of one or more of the emission spectrum of the fluorophore, the excitation spectrum of the fluorophore, the quantum yield of the fluorophore and the extinction coefficient of the fluorophore. In some instances, the memory includes instructions for simulating a spectral spillover parameter for each of the plurality of fluorophores by computer modeling or computational approximation of system component responsivity, intensity and sensitivity, including but not limited to photodetectors, excitation lasers, optical relay components (e.g., fiber optics) and fixed sources of system component noise.

In some instances, the subject systems include memory having instructions for simulating spectral parameters of one or more of the plurality of fluorophores and instructions for generating a synthetic spectral spillover spreading matrix based on the simulated spectral parameters of the fluorophores. In these embodiments, the memory includes instructions for calculating the spectral spillover spreading parameters for each of the plurality of fluorophores from the simulated spectral parameters using the generated synthetic matrix. In some embodiments, the memory includes instructions for calculating a sum of each row of the generated synthetic spectral spillover spreading matrix. In certain instances, the sum of each row of the generated synthetic spectral spillover spreading matrix is an approximation of the spectral spillover spread by each individual fluorophore into the plurality of fluorophores. In other embodiments, the memory includes instructions for calculating a sum of each column of the generated synthetic spectral spillover spreading matrix. In certain instances, the sum of each column of the generated synthetic spectral spillover spreading matrix is an approximation of the spectral spillover spread by the plurality of fluorophores into each individual fluorophore.

In some embodiments, the memory includes instructions for calculating a spectral spillover spreading parameter for each of the plurality of fluorophores with a combination of measured spectral parameters and simulated spectral parameters. For example, the memory may include instructions for applying experimentally measured spectral parameters for one or more of the fluorophores and instructions for applying simulated spectral parameters for one or more of the fluorophores in the matrix. Depending on the number of fluorophores being characterized, the generated spectral spillover spreading matrix may include one or more experimentally determined fluorescence spillover spreading values, such as 2 or more, such as 3 or more, such as 4 or more, such as 5 or more, such as 6 or more, such as 7 or more, such as 8 or more, such as 9 or more, such as 10 or more, such as 15 or more, such as 20 or more and including 25 or more. In other instances, the generated spectral spillover spreading matrix may include one or more simulated fluorescence spillover spreading values, such as 2 or more, such as 3 or more, such as 4 or more, such as 5 or more, such as 6 or more, such as 7 or more, such as 8 or more, such as 9 or more, such as 10 or more, such as 15 or more, such as 20 or more and including 25 or more. In one example, 5% or more of the fluorescence spillover spreading values in the generated spectral spillover spreading matrix are simulated values, such as 10% or more, such as 20% or more, such as 30% or more, such as 40% or more, such as 50% or more, such as 60% or more, such as 70% or more, such as 80% or more, such as 90% or more and including where 95% or more of the fluorescence spillover spreading values in the generated spectral spillover spreading matrix are simulated values. In another example, 5% or more of the fluorescence spillover spreading values in the generated spectral spillover spreading matrix are experimentally determined values, such as 10% or more, such as 20% or more, such as 30% or more, such as 40% or more, such as 50% or more, such as 60% or more, such as 70% or more, such as 80% or more, such as 90% or more and including where 95% or more of the fluorescence spillover spreading values in the generated spectral spillover spreading matrix are experimentally determined values.

In embodiments, systems may include memory having stored thereon the parameters of one or more biomolecules (e.g., population density, biomarker expression rate). In certain embodiments, the memory may include parameters of antibodies specific for one or more biomarkers on a biological cell, such as an immune cell. In some embodiments, the memory includes parameters of cluster of differentiation protein biomarkers, such as a CD biomarker for stem cells (e.g., CD34+, CD31−, CD117), such as a CD biomarker for leukocyte groups (e.g., CD45+), such as a CD biomarker for granulocytes (e.g., CD45+, CD11b, CD15+, CD24+, CD114+, CD182+), such as a CD biomarker for monocytes (e.g., CD4, CD45+, CD14+, CD114+, CD11a, CD11b, CD91+, CD16+), such as a CD biomarker for T lymphocytes (e.g., CD45+, CD3+), such as a CD biomarker for T helper cells (e.g., CD45+, CD3+, CD4+), such as a CD biomarker for T regulatory cells (e.g., CD4, CD25, FOXP3 (a transcription factor)), such as a CD biomarker for cytotoxic T cells (e.g., CD45+, CD3+, CD8+), such as a CD biomarker for B lymphocytes (e.g., CD45+, CD19+, CD20+, CD24+, CD38, CD22), such as a CD biomarker for thrombocytes (e.g., CD45+, CD61+), such as a CD biomarker for natural killer cells (e.g., CD16+, CD56+, CD3−, CD31, CD30, CD38). In certain embodiments, biomolecules of interest are specific for an antigen selected from one or more of CD3, CD4, CD8, CD16, CD27, CD45, CD56, CD69 and CD335.

In embodiments, systems include a processor with memory having instructions stored thereon, which when executed by the processor, cause the processor to pair fluorophores with biomolecules to generate a plurality of different fluorophore-biomolecule reagent pairs. In some embodiments, the memory includes instructions for pairing each biomolecule with 1 or more different fluorophores, such as 2 or more different fluorophores, such as 3 or more different fluorophores, such as 4 or more different fluorophores, such as 5 or more different fluorophores, such as 6 or more different fluorophores, such as 7 or more different fluorophores, such as 8 or more different fluorophores, such as 9 or more different fluorophores, such as 10 or more different fluorophores, such as 15 or more different fluorophores, such as 20 or more different fluorophores, such as 25 or more different fluorophores, such as 30 or more different fluorophores, such as 35 or more different fluorophores, such as 40 or more different fluorophores, such as 45 or more different fluorophores and including pairing each biomolecule with 45 or more different fluorophores to generate the plurality of different fluorophore-biomolecule reagent pairs. In embodiments, the systems includes memory having instructions stored thereon, which when executed by the processor, cause the processor to pair each fluorophore with a biomolecule that is specific for a biomarker of a cell in the sample. In some embodiments, the memory includes instructions for calculating an adjusted spillover spreading matrix for the fluorophore-biomolecule reagent pairs based on the spectral spillover spreading parameter of each fluorophore and a biomarker classification parameter. In some embodiments, the biomarker classification parameter includes a quantitative population density component for each biomarker in the sample. In some instances, the quantitative population density is a numerical range of the population of each biomarker in the sample. In other instances, the biomarker classification parameter is a semi-quantitative population density classification for each biomarker in the sample. For example, the semi-quantitative population density classification may be a designation of biomarker expression, such as where the designation of biomarker expression is 1) very high biomarker expression; 2) high biomarker expression; 3) medium biomarker expression; 4) low biomarker expression and 5) absent biomarker expression. In yet other instances, the biomarker classification parameter includes a qualitative population density classification for each biomarker in the sample. In certain instances, the qualitative population density classification for each biomarker in the sample is a binary biomarker classification. In one example, the binary biomarker classification may be a designation according to whether a biomarker is present or absent. In another example, the binary biomarker classification may be a designation according to whether a biomarker is expected to be present in the sample above a predetermined threshold (e.g., a minimum antigen density). In yet another example, the binary biomarker classification may be a designation of the criticality of the biomarker to identified set of fluorophore-biomolecule reagent pairs. For instances, the binary biomarker classification may be a designation of a biomarker as being 1) critical or 2) non-critical to the identified set of fluorophore-biomolecule reagent pairs.

In certain embodiments, the memory includes instructions for generating an adjusted spillover spreading matrix by calculating an adjusted spillover spreading parameter value (SS value, described above) of a fluorophore based on a population density value of a biomarker. In some instances, the adjusted SS values describe the amount of excess spillover spreading in the measured value of a first fluorophore (i.e., "receiving" fluorophore) due to fluorescence of a second, different fluorophore (i.e., a spillover "source" fluorophore). In certain instances, the standard deviation of the first fluorophore increases proportionally to the square root of the expression level of the second fluorophore.

In some embodiments, systems include memory having instructions for calculating an adjusted spillover spreading parameter based on a population density value of a biomarker, where the instructions include: (1) multiplying the spillover spreading parameter value (SS value) by the square root of the population density value of the biomarker of the second fluorophore to generate a standard deviation in expression of the first fluorophore, and (2) dividing the adjusted spillover spreading parameter value (SS value) by the population density value of a biomarker of the first fluorophore to generate a count value (CV). In some instances, the count value describes spillover spread in the first fluorophore relative to expression level of the first fluorophore.

In certain embodiments, the memory includes instructions for calculating a total spillover spreading parameter into a fluorophore from a plurality of fluorophores based on population density values of a plurality of biomarkers. In some instances, the memory includes instructions for generating a matrix of the spillover spreading parameter values where each row of the matrix corresponds to a first fluorophore (e.g., a spillover source fluorophore) and each column corresponds to a second fluorophore (e.g., a spillover receiving fluorophore), so that the values in the matrix (e.g., entry in row i and column j) correspond to an increased standard deviation in expression of the first fluorophore (e.g., fluorophore j) per square root unit of expression of the second fluorophore (e.g. fluorophore i). In certain instances, the memory includes instructions for determining a total spillover spreading parameter of the fluorophore from the plurality of fluorophores by: 1) calculating the sum of squared adjusted spillover spreading parameter values for each fluorophore; 2) determining the square root of the sum of squared adjusted spillover spreading parameter values to generate a standard deviation or CV of the fluorophore.

In certain embodiments, the memory includes instructions which when executed by the processor, cause the processor to calculate a total spillover spreading parameter of a fluorophore from a generated spillover spreading matrix by: 1) calculating a sum of squared adjusted spillover spreading values in a column corresponding to a second fluorophore and 2) determining a square root of the sum of squared adjusted spillover spreading values in the column. In certain instances, a total spillover spreading parameter of a fluorophore is calculated from a generated spillover spreading matrix according to:

$$ColSum = \frac{1}{AgDens_{col}} \left( \sum_{row=1}^{N_{rows}} AgDens_{row}(SS_{col}^{row})^2 \right)^{1/2}$$

Systems of interest include memory having instructions stored thereon, which when executed by the processor, cause the processor to identify an optimal set of fluorophore-biomolecule reagent pairs for characterizing the sample by flow cytometry. In some embodiments, the memory includes instructions for identifying the optimal set of fluorophore-biomolecule reagent pairs with a reagent pair ranking algorithm, such as where the memory includes instructions for assigning a score to each of the fluorophore-biomolecule reagent pairs based on the calculated adjusted spillover spreading matrix value for each fluorophore-biomolecule reagent pair. In some embodiments, the memory includes instructions for identifying the optimal set of fluorophore-biomolecule reagent pairs by selecting the fluorophore-biomolecule reagent pairs having the lowest score based on the calculated adjusted spillover spreading matrix. In other embodiments, the memory includes instructions for identifying the optimal set of fluorophore-biomolecule reagent pairs by selecting the fluorophore-biomolecule reagent pairs having a score that is below a predetermined threshold based on the calculated adjusted spillover spreading matrix. In yet other embodiments, the memory includes instructions for identifying the optimal set of fluorophore-biomolecule reagent pairs by selecting at random a predetermined number of the fluorophore-biomolecule reagent pairs.

In other embodiments, systems include memory having instructions for identifying the optimal set of fluorophore-biomolecule reagent pairs by applying a constrained optimization algorithm, such as where each fluorophore-biomolecule reagent pair is selected at random and subjected to a set of constraints to generate a constrained set of fluorophore-biomolecule reagent pairs. In certain embodiments, the constrained optimization algorithm implemented by the memory of the subject system includes solving a constrained optimization problem (COP). In other embodiments, the constrained optimization algorithm includes solving a constrained satisfaction problem (CSP). In certain instances, the constrained optimization algorithm includes a constraint satisfaction algorithm in which fluorophore-biomolecule reagent pairs are selected to satisfy a predetermined constraint such that each fluorophore-biomolecule reagent pair does not cause excess spillover spreading into other fluorophore-biomolecule reagent pairs in a predetermined subpopulation. In certain embodiments, the memory includes instructions for identifying the optimal set of fluorophore-biomolecule reagent pairs by applying an iterative genetic algorithm.

Figure 3:
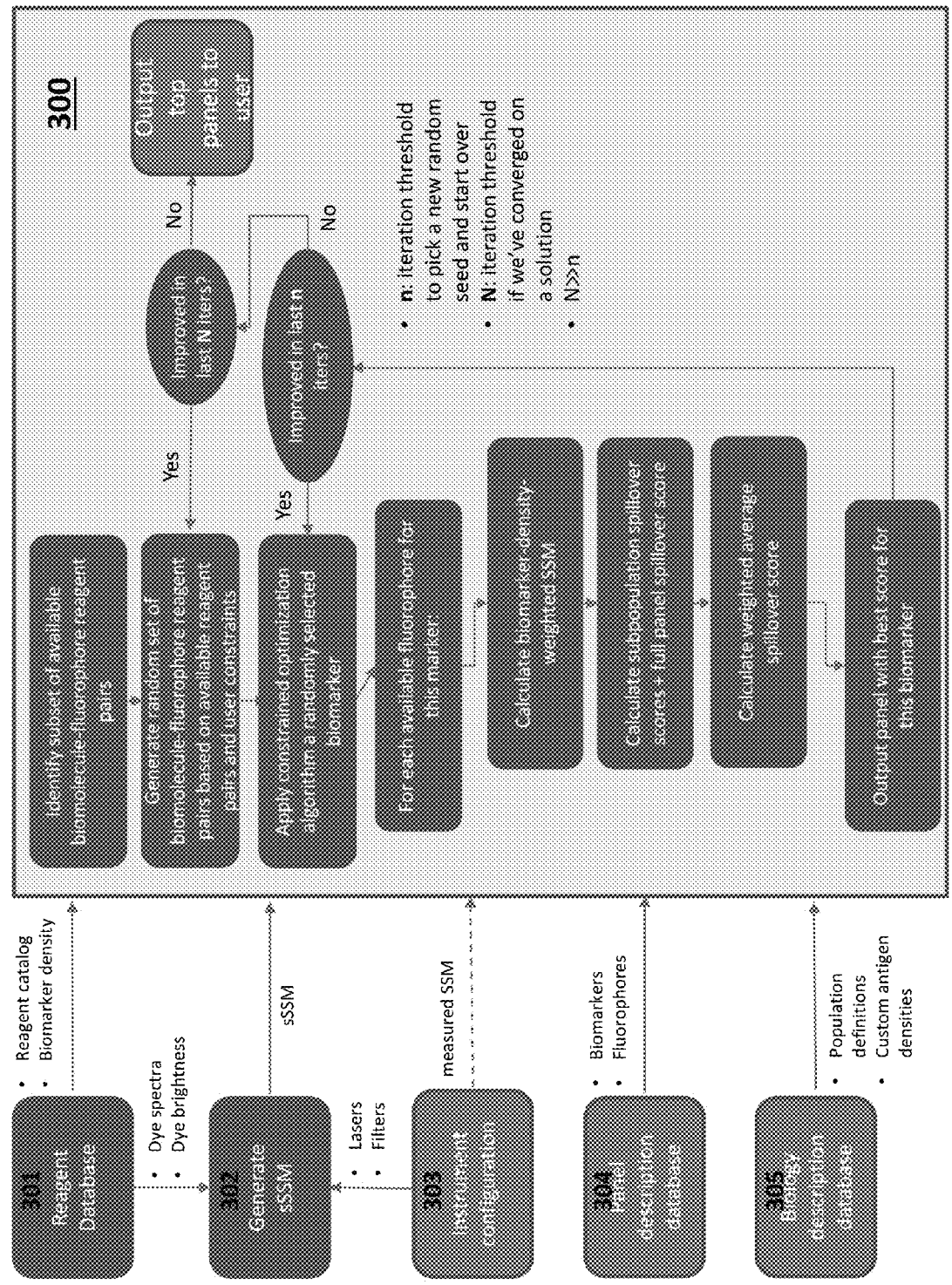
FIG. 3 depicts a system with algorithm for identifying a set of fluorophore-biomolecule reagent pairs according to certain embodiments.

FIG. 3 depicts a system configured with algorithm for identifying an optimal set of fluorophore-biomolecule reagent pairs according to certain embodiments. Processing system 300 is in operable communication with reagent database 301 which includes a reagent catalog of available fluorophores and biomarker density data. A user can input parameters (or select from a pull-down menu) into processing system 300 of the paired fluorophore-biomolecule reagent pairs from panel description 304 and biology description 305. A synthetic spillover spreading matrix can be generated based on parameters of the irradiation and detection systems (e.g., lasers, photodetectors, filters, etc.) received from system configurations memory 303 and spectral parameters of the fluorophores received from reagent database 301. A measured spillover spreading matrix can also be generated and inputted into processing system 300. Processing system 300 includes memory having algorithm for identifying a subset of available biomolecule-fluorophore reagent pairs; algorithm for generating a random set of biomolecule-fluorophore reagent pairs based on available reagent pairs and user constraints; algorithm for applying one or more minimal conflict constraints with a randomly selected biomarker; algorithm for calculating a biomarker classification parameter (e.g., biomarker density) weighted spillover spreading matrix; algorithm for calculating subpopulation spillover scores and a spillover score for the full set of identified biomolecule-fluorophore reagent pairs; algorithm for calculating a weighted average spillover score and algorithm for outputting an identified panel for each biomarker. Processing system 300 is configured to iteratively apply the algorithm for scoring panels of biomolecule-fluorophore reagent pairs until an optimal panel is identified and outputted to a user.

Systems according to some embodiments, may include a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low-level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques. The processor may be any suitable analog or digital system. In some embodiments, the processor includes analog electronics which provide feedback control, such as for example negative feedback control.

The system memory may be any of a variety of known or future memory storage devices. Examples include any commonly available random-access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid-state storage devices (including magnetic or optical disks or tape or RAM, or any other suitable device, either fixed or portable). The processor may include a general-purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra-Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the subject systems and other external devices such as a computer terminal (for example, at a physician's office or in hospital environment) that is configured for similar complementary data communication.

In one embodiment, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows 10, Windows NT®, Windows XP, Windows 7, Windows 8, iOS, Sun Solaris, Linux, OS/400, Compaq Tru64 Unix, SGI IRIX, Siemens Reliant Unix, Ubuntu, Zorin OS and others.

Figure 4:
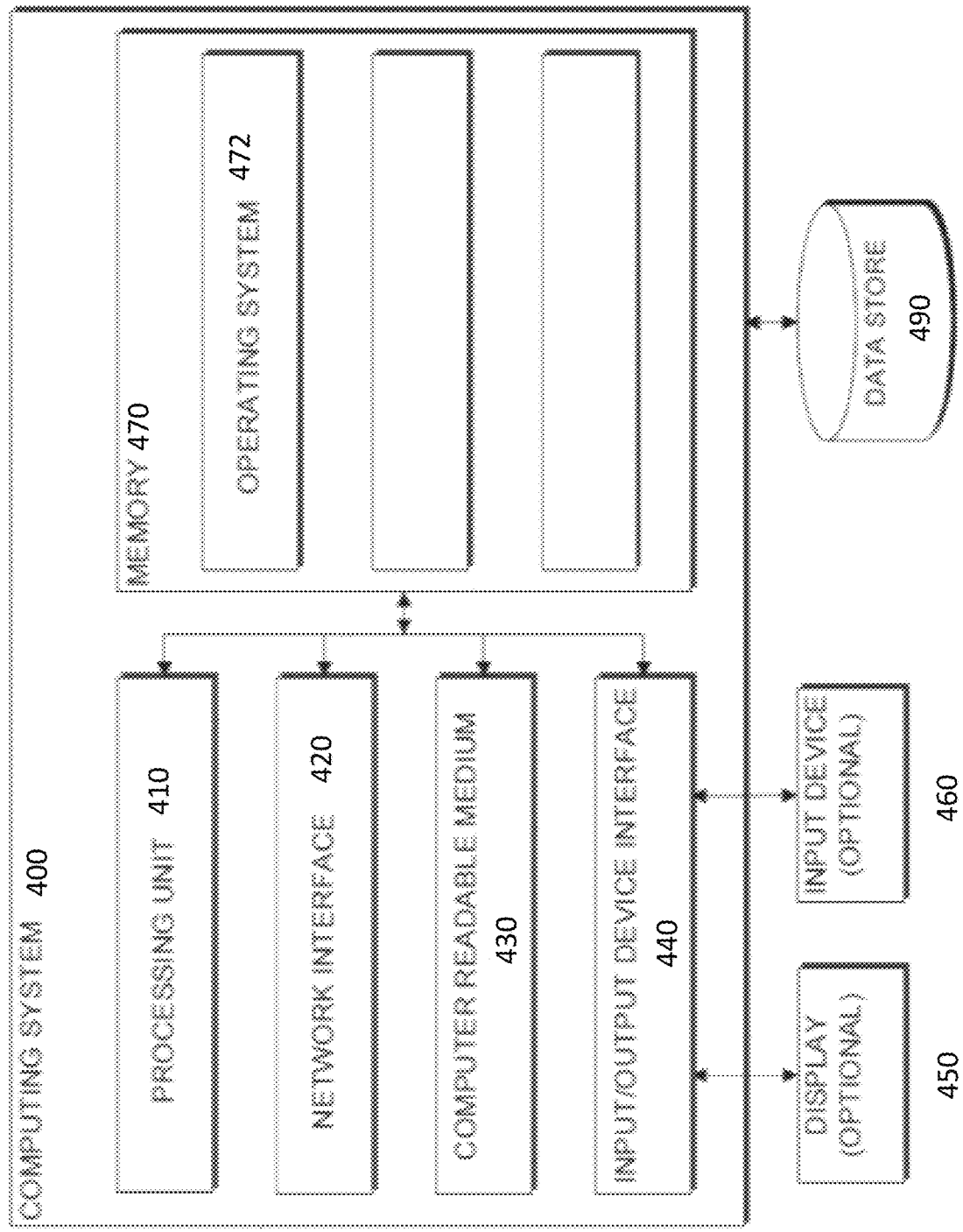
FIG. 4 depicts a block diagram of a computing system according to certain embodiments.

FIG. 4 depicts a general architecture of an example computing device 400 according to certain embodiments. The general architecture of the computing device 400 depicted in FIG. 4 includes an arrangement of computer hardware and software components. The computing device 400 may include many more (or fewer) elements than those shown in FIG. 4. It is not necessary, however, that all of these generally conventional elements be shown in order to provide an enabling disclosure. As illustrated, the computing device 400 includes a processing unit 410, a network interface 420, a computer readable medium drive 430, an input/output device interface 440, a display 450, and an input device 460, all of which may communicate with one another by way of a communication bus. The network interface 420 may provide connectivity to one or more networks or computing systems. The processing unit 410 may thus receive information and instructions from other computing systems or services via a network. The processing unit 410 may also communicate to and from memory 470 and further provide output information for an optional display 450 via the input/output device interface 440. The input/output device interface 440 may also accept input from the optional input device 460, such as a keyboard, mouse, digital pen, microphone, touch screen, gesture recognition system, voice recognition system, gamepad, accelerometer, gyroscope, or other input device.

The memory 470 may contain computer program instructions (grouped as modules or components in some embodiments) that the processing unit 410 executes in order to implement one or more embodiments. The memory 470 generally includes RAM, ROM and/or other persistent, auxiliary or non-transitory computer-readable media. The memory 470 may store an operating system 472 that provides computer program instructions for use by the processing unit 410 in the general administration and operation of the computing device 400. The memory 470 may further include computer program instructions and other information for implementing aspects of the present disclosure.

Figure 5A:
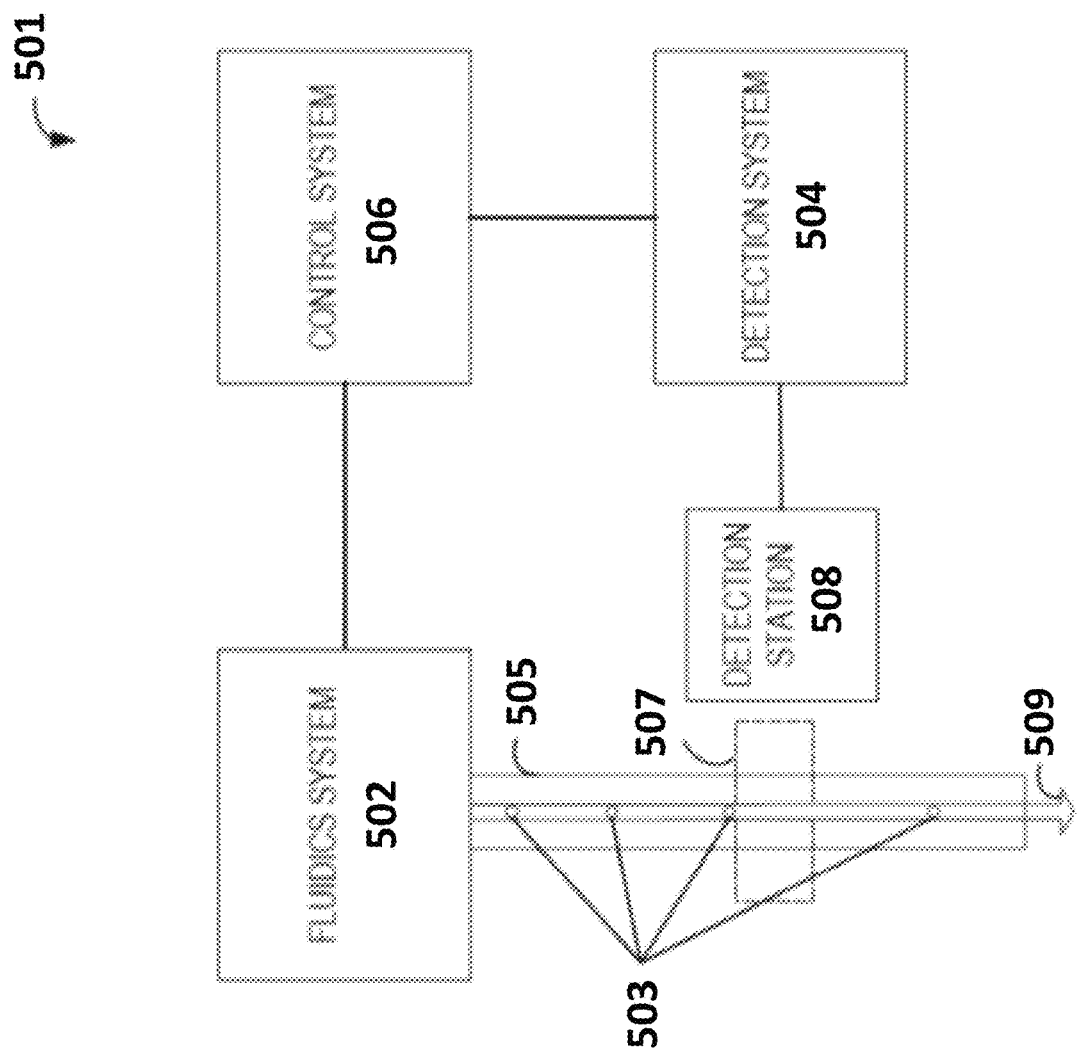
FIG. 5A depicts a functional block diagram of a particle analysis system for computational based sample analysis and particle characterization according to certain embodiments.

In some embodiments, the subject systems are part of or are incorporated into a particle analyzer where the particle analysis system 501 (FIG. 5A) can be used to analyze and characterize particles, with or without physically sorting the particles into collection vessels. FIG. 5A shows a functional block diagram of a particle analysis system for computational based sample analysis and particle characterization. In some embodiments, the particle analysis system 501 is a flow system. The particle analysis system 501 shown in FIG. 5A can be configured to perform, in whole or in part, the methods described herein. The particle analysis system 501 includes a fluidics system 502. The fluidics system 502 can include or be coupled with a sample tube 505 and a moving fluid column within the sample tube in which particles 503 (e.g. cells) of a sample move along a common sample path 509.

The particle analysis system 501 includes a detection system 504 configured to collect a signal from each particle as it passes one or more detection stations along the common sample path. A detection station 508 generally refers to a monitored area 507 of the common sample path. Detection can, in some implementations, include detecting light or one or more other properties of the particles 503 as they pass through a monitored area 507. In FIG. 5A, one detection station 508 with one monitored area 507 is shown. Some implementations of the particle analysis system 501 can include multiple detection stations. Furthermore, some detection stations can monitor more than one area.

Each signal is assigned a signal value to form a data point for each particle. As described above, this data can be referred to as event data. The data point can be a multidimensional data point including values for respective properties measured for a particle. The detection system 504 is configured to collect a succession of such data points in a first time interval.

The particle analysis system 501 can also include a control system 506. The control system 506 can include one or more processors, an amplitude control circuit and/or a frequency control circuit. The control system shown can be operationally associated with the fluidics system 502. The control system can be configured to generate a calculated signal frequency for at least a portion of the first time interval based on a Poisson distribution and the number of data points collected by the detection system 504 during the first time interval. The control system 506 can be further configured to generate an experimental signal frequency based on the number of data points in the portion of the first time interval. The control system 406 can additionally compare the experimental signal frequency with that of a calculated signal frequency or a predetermined signal frequency.

Figure 5B:
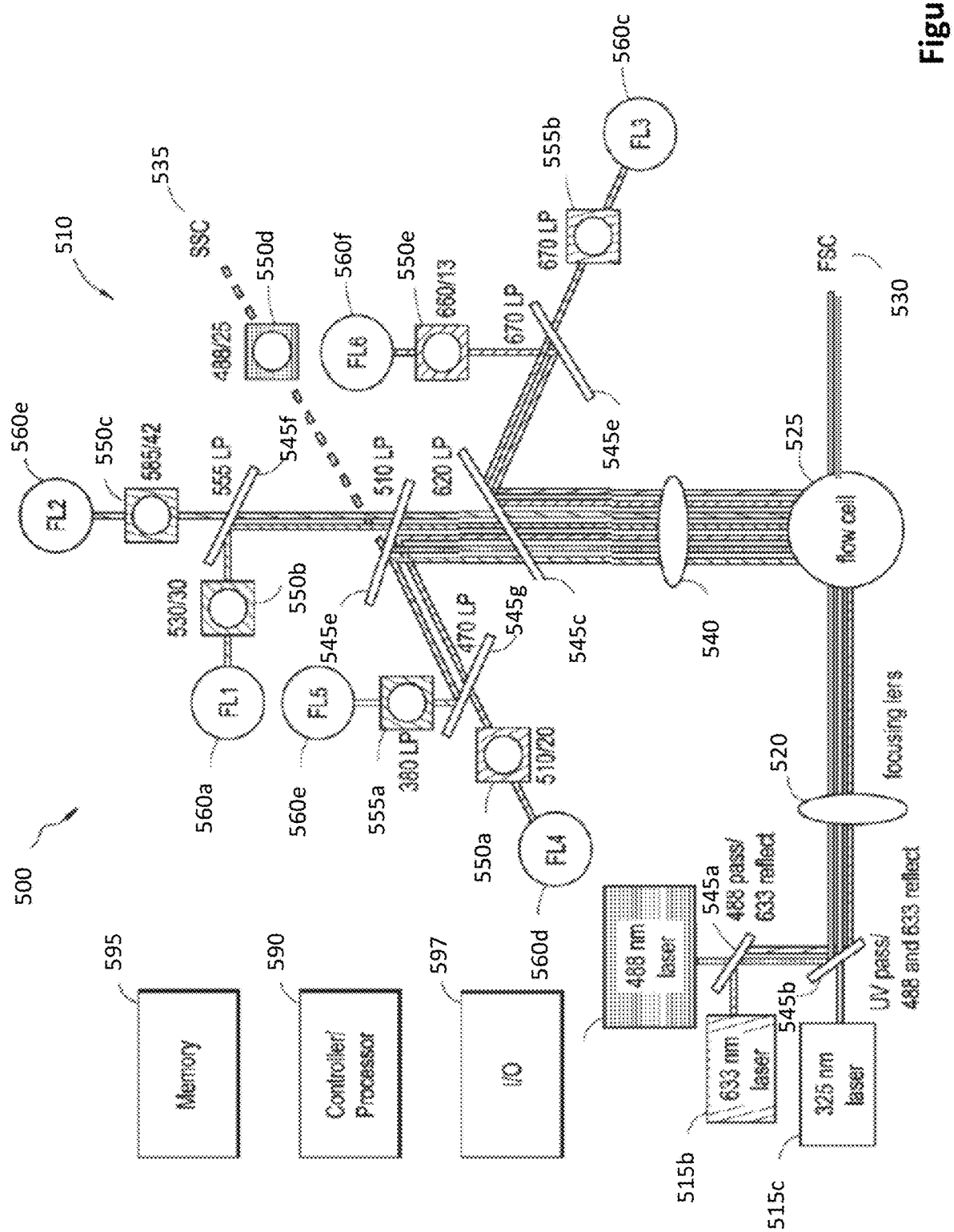
FIG. 5B depicts a flow cytometer according to certain embodiments.

FIG. 5B shows a system 500 for flow cytometry in accordance with an illustrative embodiment of the present invention. The system 500 includes a flow cytometer 510, a controller/processor 590 and a memory 595. The flow cytometer 510 includes one or more excitation lasers 515*a*-515*c*, a focusing lens 520, a flow chamber 525, a forward scatter detector 530, a side scatter detector 535, a fluorescence collection lens 540, one or more beam splitters 545*a*-545*g*, one or more bandpass filters 550*a*-550*e*, one or more longpass ("LP") filters 555*a*-555*b*, and one or more fluorescent detectors 560*a*-560*f*.

The excitation lasers 515*a*-*c* emit light in the form of a laser beam. The wavelengths of the laser beams emitted from excitation lasers 515*a*-515*c* are 488 nm, 633 nm, and 325 nm, respectively, in the example system of FIG. 4B. The laser beams are first directed through one or more of beam splitters 545*a* and 545*b*. Beam splitter 445*a* transmits light at 488 nm and reflects light at 633 nm. Beam splitter 545*b* transmits UV light (light with a wavelength in the range of 10 to 400 nm) and reflects light at 488 nm and 633 nm.

The laser beams are then directed to a focusing lens 520, which focuses the beams onto the portion of a fluid stream where particles of a sample are located, within the flow chamber 525. The flow chamber is part of a fluidics system which directs particles, typically one at a time, in a stream to the focused laser beam for interrogation. The flow chamber can comprise a flow cell in a benchtop cytometer or a nozzle tip in a stream-in-air cytometer.

The light from the laser beam(s) interacts with the particles in the sample by diffraction, refraction, reflection, scattering, and absorption with re-emission at various different wavelengths depending on the characteristics of the particle such as its size, internal structure, and the presence of one or more fluorescent molecules attached to or naturally present on or in the particle. The fluorescence emissions as well as the diffracted light, refracted light, reflected light, and scattered light may be routed to one or more of the forward scatter detector 530, the side scatter detector 535, and the one or more fluorescent detectors 560*a*-560*f* through one or more of the beam splitters 545*a*-545*g*, the bandpass filters 550*a*-550*e*, the longpass filters 555*a*-555*b*, and the fluorescence collection lens 540.

The fluorescence collection lens 540 collects light emitted from the particle-laser beam interaction and routes that light towards one or more beam splitters and filters. Bandpass filters, such as bandpass filters 550*a*-550*e*, allow a narrow range of wavelengths to pass through the filter. For example, bandpass filter 550*a* is a 510/20 filter. The first number represents the center of a spectral band. The second number provides a range of the spectral band. Thus, a 510/20 filter extends 10 nm on each side of the center of the spectral band, or from 500 nm to 520 nm. Shortpass filters transmit wavelengths of light equal to or shorter than a specified wavelength. Longpass filters, such as longpass filters 555*a*-555*b*, transmit wavelengths of light equal to or longer than a specified wavelength of light. For example, longpass filter 555*a*, which is a 670 nm longpass filter, transmits light equal to or longer than 670 nm. Filters are often selected to optimize the specificity of a detector for a particular fluorescent dye. The filters can be configured so that the spectral band of light transmitted to the detector is close to the emission peak of a fluorescent dye.

Beam splitters direct light of different wavelengths in different directions. Beam splitters can be characterized by filter properties such as shortpass and longpass. For example, beam splitter 545*g* is a 620 SP beam splitter, meaning that the beam splitter 545*g* transmits wavelengths of light that are 620 nm or shorter and reflects wavelengths of light that are longer than 620 nm in a different direction. In one embodiment, the beam splitters 545*a*-545*g* can comprise optical mirrors, such as dichroic mirrors.

The forward scatter detector 530 is positioned slightly off axis from the direct beam through the flow cell and is configured to detect diffracted light, the excitation light that travels through or around the particle in mostly a forward direction. The intensity of the light detected by the forward scatter detector is dependent on the overall size of the particle. The forward scatter detector can include a photodiode. The side scatter detector 535 is configured to detect refracted and reflected light from the surfaces and internal structures of the particle, and tends to increase with increasing particle complexity of structure. The fluorescence emissions from fluorescent molecules associated with the particle can be detected by the one or more fluorescent detectors 560*a*-560*f*. The side scatter detector 535 and fluorescent detectors can include photomultiplier tubes. The signals detected at the forward scatter detector 530, the side scatter detector 535 and the fluorescent detectors can be converted to electronic signals (voltages) by the detectors. This data can provide information about the sample.

One of skill in the art will recognize that a flow cytometer in accordance with an embodiment of the present invention is not limited to the flow cytometer depicted in FIG. 5B, but can include any flow cytometer known in the art. For example, a flow cytometer may have any number of lasers, beam splitters, filters, and detectors at various wavelengths and in various different configurations.

In operation, cytometer operation is controlled by a controller/processor 590, and the measurement data from the detectors can be stored in the memory 595 and processed by the controller/processor 590. Although not shown explicitly, the controller/processor 590 is coupled to the detectors to receive the output signals therefrom, and may also be coupled to electrical and electromechanical components of the flow cytometer 500 to control the lasers, fluid flow parameters, and the like. Input/output (I/O) capabilities 597 may be provided also in the system. The memory 595, controller/processor 590, and I/O 597 may be entirely provided as an integral part of the flow cytometer 510. In such an embodiment, a display may also form part of the I/O capabilities 597 for presenting experimental data to users of the cytometer 500. Alternatively, some or all of the memory 595 and controller/processor 590 and I/O capabilities may be part of one or more external devices such as a general purpose computer. In some embodiments, some or all of the memory 595 and controller/processor 590 can be in wireless or wired communication with the cytometer 510. The controller/processor 590 in conjunction with the memory 595 and the I/O 597 can be configured to perform various functions related to the preparation and analysis of a flow cytometer experiment.

The system illustrated in FIG. 5B includes six different detectors that detect fluorescent light in six different wavelength bands (which may be referred to herein as a "filter window" for a given detector) as defined by the configuration of filters and/or splitters in the beam path from the flow cell 525 to each detector. Different fluorescent molecules used for a flow cytometer experiment will emit light in their own characteristic wavelength bands. The particular fluorescent labels used for an experiment and their associated fluorescent emission bands may be selected to generally coincide with the filter windows of the detectors. However, as more detectors are provided, and more labels are utilized, perfect correspondence between filter windows and fluorescent emission spectra is not possible. It is generally true that although the peak of the emission spectra of a particular fluorescent molecule may lie within the filter window of one particular detector, some of the emission spectra of that label will also overlap the filter windows of one or more other detectors. This may be referred to as spillover. The I/O 597 can be configured to receive data regarding a flow cytometer experiment having a panel of fluorescent labels and a plurality of cell populations having a plurality of markers, each cell population having a subset of the plurality of markers. The I/O 597 can also be configured to receive biological data assigning one or more markers to one or more cell populations, marker density data, emission spectrum data, data assigning labels to one or more markers, and cytometer configuration data. Flow cytometer experiment data, such as label spectral characteristics and flow cytometer configuration data can also be stored in the memory 595. The controller/processor 590 can be configured to evaluate one or more assignments of labels to markers.

Figure 6:
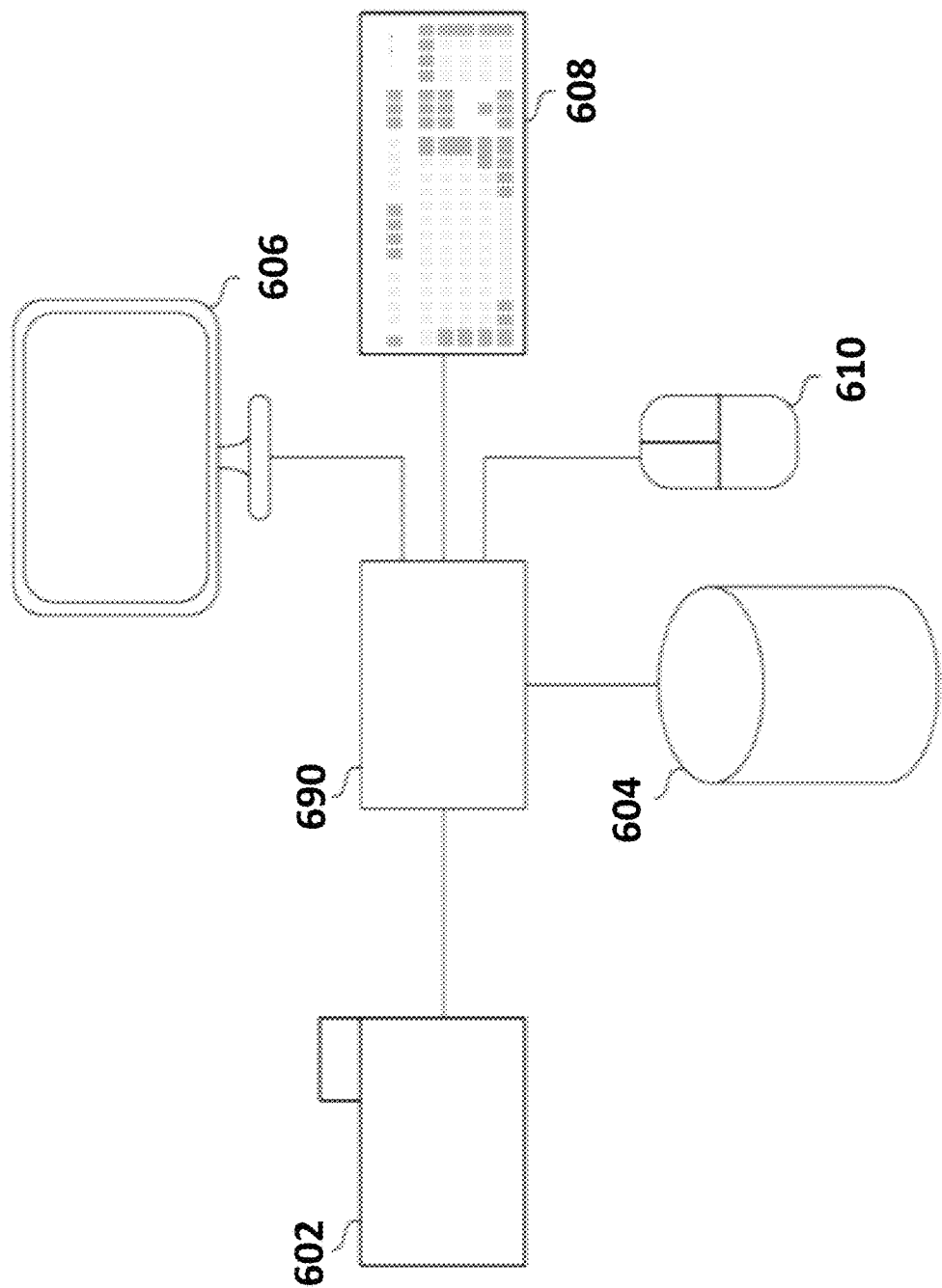
FIG. 6 depicts a functional block diagram for one example of a particle analyzer control system according to certain embodiments.

FIG. 6 shows a functional block diagram for one example of a particle analyzer control system, such as an analytics controller 600, for analyzing and displaying biological events. An analytics controller 600 can be configured to implement a variety of processes for controlling graphic display of biological events.

A particle analyzer 602 can be configured to acquire biological event data. For example, a flow cytometer can generate flow cytometric event data. The particle analyzer 602 can be configured to provide biological event data to the analytics controller 600. A data communication channel can be included between the particle analyzer 602 and the analytics controller 600. The biological event data can be provided to the analytics controller 600 via the data communication channel.

The analytics controller 600 can be configured to receive biological event data from the particle analyzer 602. The biological event data received from the particle analyzer 602 can include flow cytometric event data. The analytics controller 600 can be configured to provide a graphical display including a first plot of biological event data to a display device 606. The analytics controller 600 can be further configured to render a region of interest as a gate around a population of biological event data shown by the display device 606, overlaid upon the first plot, for example. In some embodiments, the gate can be a logical combination of one or more graphical regions of interest drawn upon a single parameter histogram or bivariate plot. In some embodiments, the display can be used to display particle parameters or saturated detector data.

The analytics controller 600 can be further configured to display the biological event data on the display device 606 within the gate differently from other events in the biological event data outside of the gate. For example, the analytics controller 600 can be configured to render the color of biological event data contained within the gate to be distinct from the color of biological event data outside of the gate. The display device 606 can be implemented as a monitor, a tablet computer, a smartphone, or other electronic device configured to present graphical interfaces.

The analytics controller 600 can be configured to receive a gate selection signal identifying the gate from a first input device. For example, the first input device can be implemented as a mouse 610. The mouse 610 can initiate a gate selection signal to the analytics controller 500 identifying the gate to be displayed on or manipulated via the display device 606 (e.g., by clicking on or in the desired gate when the cursor is positioned there). In some implementations, the first device can be implemented as the keyboard 608 or other means for providing an input signal to the analytics controller 600 such as a touchscreen, a stylus, an optical detector, or a voice recognition system. Some input devices can include multiple inputting functions. In such implementations, the inputting functions can each be considered an input device. For example, as shown in FIG. 6, the mouse 610 can include a right mouse button and a left mouse button, each of which can generate a triggering event.

The triggering event can cause the analytics controller 600 to alter the manner in which the data is displayed, which portions of the data is actually displayed on the display device 606, and/or provide input to further processing such as selection of a population of interest for particle sorting.

In some embodiments, the analytics controller 600 can be configured to detect when gate selection is initiated by the mouse 610. The analytics controller 600 can be further configured to automatically modify plot visualization to facilitate the gating process. The modification can be based on the specific distribution of biological event data received by the analytics controller 600.

The analytics controller 600 can be connected to a storage device 604. The storage device 604 can be configured to receive and store biological event data from the analytics controller 600. The storage device 604 can also be configured to receive and store flow cytometric event data from the analytics controller 600. The storage device 604 can be further configured to allow retrieval of biological event data, such as flow cytometric event data, by the analytics controller 600.

A display device 606 can be configured to receive display data from the analytics controller 600. The display data can comprise plots of biological event data and gates outlining sections of the plots. The display device 606 can be further configured to alter the information presented according to input received from the analytics controller 600 in conjunction with input from the particle analyzer 602, the storage device 604, the keyboard 608, and/or the mouse 610.

In some implementations, the analytics controller 600 can generate a user interface to receive example events for sorting. For example, the user interface can include a control for receiving example events or example images. The example events or images or an example gate can be provided prior to collection of event data for a sample, or based on an initial set of events for a portion of the sample.

In certain embodiments, the subject systems are part of or are incorporated into a flow cytometric system. Suitable flow cytometry systems may include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem. January;* 49(pt 1):17-28; Linden, et. al., *Semin Throm Hemost.* 2004 October; 30(5):502-11; Alison, et al. *J Pathol,* 2010 December; 222(4):335-344; and Herbig, et al. (2007) *Crit Rev Ther Drug Carrier Syst.* 24(3): 203-255; the disclosures of which are incorporated herein by reference. In certain instances, flow cytometry systems of interest include BD Biosciences FACSCanto™ II flow cytometer, BD Accuri™ flow cytometer, BD Biosciences FACSCelesta™ flow cytometer, BD Biosciences FACSLyric™ flow cytometer, BD Biosciences FACSVerse™ flow cytometer, BD Biosciences FACSymphony™ flow cytometer BD Biosciences LSRFortessa™ flow cytometer, BD Biosciences LSRFortess™ X-20 flow cytometer and BD Biosciences FACSCalibur™ cell sorter, a BD Biosciences FACSCount™ cell sorter, BD Biosciences FACSLyric™ cell sorter and BD Biosciences Via™ cell sorter BD Biosciences Influx™ cell sorter, BD Biosciences Jazz™ cell sorter, BD Biosciences Aria™ cell sorters and BD Biosciences FACSMelody™ cell sorter, or the like.

In certain embodiments, the subject flow cytometric systems are configured to sort one or more of the particles (e.g., cells) of the sample. The term "sorting" is used herein in its conventional sense to refer to separating components (e.g., cells, non-cellular particles such as biological macromolecules) of the sample and in some instances delivering the separated components to one or more sample collection containers. For example, the subject systems may be configured for sorting samples having 2 or more components, such as 3 or more components, such as 4 or more components, such as 5 or more components, such as 10 or more components, such as 15 or more components and including soring a sample having 25 or more components. One or more of the sample components may be separated from the sample and delivered to a sample collection container, such as 2 or more sample components, such as 3 or more sample components, such as 4 or more sample components, such as 5 or more sample components, such as 10 or more sample components and including 15 or more sample components may be separated from the sample and delivered to a sample collection container.

In some embodiments, particle sorting systems of interest are configured to sort particles with an enclosed particle sorting module, such as those described in U.S. Patent Publication No. 2017/0299493, filed on Mar. 28, 2017, the disclosure of which is incorporated herein by reference. In certain embodiments, particles (e.g., cells) of the sample are sorted using a sort decision module having a plurality of sort decision units, such as those described in U.S. patent application Ser. No. 16/725,756, filed on Dec. 23, 2019, the disclosure of which is incorporated herein by reference. In some embodiments, the subject particle sorting systems are flow cytometric systems, such those described in U.S. Pat. Nos. 10,006,852; 9,952,076; 9,933,341; 9,784,661; 9,726,527; 9,453,789; 9,200,334; 9,097,640; 9,095,494; 9,092,034; 8,975,595; 8,753,573; 8,233,146; 8,140,300; 7,544,326; 7,201,875; 7,129,505; 6,821,740; 6,813,017; 6,809,804; 6,372,506; 5,700,692; 5,643,796; 5,627,040; 5,620,842; 5,602,039; the disclosure of which are herein incorporated by reference in their entirety.

Non-Transitory Computer-Readable Storage Medium

Aspects of the present disclosure further include non-transitory computer readable storage mediums having instructions for practicing the subject methods. Computer readable storage mediums may be employed on one or more computers for complete automation or partial automation of a system for practicing methods described herein. In certain embodiments, instructions in accordance with the methods described herein can be coded onto a computer-readable medium in the form of "programming", where the term "computer readable medium" as used herein refers to any non-transitory storage medium that participates in providing instructions and data to a computer for execution and processing. Examples of suitable non-transitory storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer. The computer-implemented method described herein can be executed using programming that can be written in one or more of any number of computer programming languages. Such languages include, for example, Java (Sun Microsystems, Inc., Santa Clara, CA), Visual Basic (Microsoft Corp., Redmond, WA), and C++ (AT&T Corp., Bedminster, NJ), as well as any many others.

Non-transitory computer readable storage medium according to certain embodiments include instructions stored thereon having algorithm for calculating a spectral spillover spreading parameter for a plurality of fluorophores, algorithm for pairing each fluorophore with a biomolecule that is specific for a biomarker of a cell in the sample to generate a plurality of fluorophore-biomolecule reagent pairs, algorithm for generating an adjusted spillover spreading matrix for the fluorophore-biomolecule reagent pairs based on the spectral spillover spreading parameter of each fluorophore and a biomarker classification parameter and algorithm for identifying an optimal set of fluorophore-biomolecule reagent pairs based on the calculated spillover spreading values from the adjusted spillover spreading matrix.

In embodiments, the non-transitory computer readable storage medium includes algorithm for calculating a spectral spillover spreading parameter for a plurality of fluorophores. In some embodiments, the non-transitory computer readable storage medium includes algorithm for calculating the spectral spillover spreading parameter by generating a matrix of fluorescence spillover spreading values for the plurality of fluorophores. Non-transitory computer readable storage medium include algorithm for calculating the fluorescence spillover spreading values in the matrix based on the fluorescence spillover spread of a fluorophore when in the presence of another fluorophore. In some embodiments, the non-transitory computer readable storage medium includes algorithm for calculating the fluorescence spillover spreading value based on the overlap of the fluorescence spectra of the two different fluorophores. In some instances, the non-transitory computer readable storage medium includes algorithm for calculating the spectral spillover spreading parameter by calculating a sum of each row of the generated matrix. In certain instances, the sum of each row of the generated matrix is an approximation of the spectral spillover spread by each individual fluorophore into the plurality of fluorophores. In other instances, the non-transitory computer readable storage medium includes algorithm for calculating the spectral spillover spreading parameter by calculating a sum of each column of the generated matrix. In certain instances, the sum of each column of the generated matrix is an approximation of the spectral spillover spread by the plurality of fluorophores into each other individual fluorophore.

In certain embodiments, the non-transitory computer readable storage medium includes algorithm for simulating the spectral spillover spreading parameter for each of the plurality of fluorophores. In some embodiments the non-transitory computer readable storage medium includes algorithm for simulating spectral properties of each fluorophore and algorithm for calculating spillover spreading values for each of the fluorophores based on the simulated spectral properties. For example, the simulated spectral properties of the fluorophore may be one or more of emission spectrum of the fluorophore, excitation spectrum of the fluorophore, quantum yield of the fluorophore and extinction coefficient of the fluorophore. In certain embodiments, the non-transitory computer readable storage medium includes algorithm for calculating the spillover spreading values for each of the fluorophores by compensation. In other embodiments, the non-transitory computer readable storage medium includes algorithm for calculating the spillover spreading values for each of the fluorophores by spectral unmixing.

In embodiments, the non-transitory computer readable storage medium includes algorithm for pairing each fluorophore with a biomolecule that is specific for a biomarker of a cell in the sample. In some embodiments, the non-transitory computer readable storage medium includes algorithm for calculating an adjusted spillover spreading matrix for the fluorophore-biomolecule reagent pairs based on the spectral spillover spreading parameter of each fluorophore and a biomarker classification parameter. In some embodiments, the biomarker classification parameter includes a quantitative population density component for each biomarker in the sample. In some instances, the quantitative population density is a numerical range of the population of each biomarker in the sample. In other instances, the biomarker classification parameter is a semi-quantitative population density classification for each biomarker in the sample. For example, the semi-quantitative population density classification may be a designation of biomarker expression, such as where the designation of biomarker expression is 1) very high biomarker expression; 2) high biomarker expression; 3) medium biomarker expression; 4) low biomarker expression and 5) absent biomarker expression. In yet other instances, the biomarker classification parameter includes a qualitative population density classification for each biomarker in the sample. In certain instances, the qualitative population density classification for each biomarker in the sample is a binary biomarker classification. In one example, the binary biomarker classification may be a designation according to whether a biomarker is present or absent. In another example, the binary biomarker classification may be a designation according to whether a biomarker is expected to be present in the sample above a predetermined threshold (e.g., a minimum antigen density). In yet another example, the binary biomarker classification may be a designation of the criticality of the biomarker to identified set of fluorophore-biomolecule reagent pairs. For instance, the binary biomarker classification may be a designation of a biomarker as being 1) critical or 2) non-critical to the identified set of fluorophore-biomolecule reagent pairs.

In certain embodiments, the non-transitory computer readable storage medium includes algorithm for generating an adjusted spillover spreading matrix by calculating an adjusted spillover spreading parameter value (SS value, described above) of a fluorophore based on a population density value of a biomarker. In some instances, the adjusted SS values describe the amount of excess spillover spreading in the measured value of a first fluorophore (i.e., "receiving" fluorophore) due to fluorescence of a second, different fluorophore (i.e., a spillover "source" fluorophore). In certain instances, the standard deviation of the first fluorophore increases proportionally to the square root of the expression level of the second fluorophore.

In some embodiments, the non-transitory computer readable storage medium includes algorithm for calculating an adjusted spillover spreading parameter based on a population density value of a biomarker, where the non-transitory computer readable storage medium includes: (1) algorithm for multiplying the spillover spreading parameter value (SS value) by the square root of the population density value of the biomarker of the second fluorophore to generate a standard deviation in expression of the first fluorophore, and (2) algorithm for dividing the adjusted spillover spreading parameter value (SS value) by the population density value of a biomarker of the first fluorophore to generate a count value (CV). In some instances, the count value describes spillover spread in the first fluorophore relative to expression level of the first fluorophore.

In certain embodiments, the non-transitory computer readable storage medium includes algorithm for calculating a total spillover spreading parameter into a fluorophore from a plurality of fluorophores based on population density values of a plurality of biomarkers. In some instances, the non-transitory computer readable storage medium includes algorithm for generating a matrix of the spillover spreading parameter values where each row of the matrix corresponds to a first fluorophore (e.g., a spillover source fluorophore) and each column corresponds to a second fluorophore (e.g., a spillover receiving fluorophore), so that the values in the matrix (e.g., entry in row i and column j) correspond to an increased standard deviation in expression of the first fluorophore (e.g., fluorophore j) per square root unit of expression of the second fluorophore (e.g. fluorophore i). In certain instances, the non-transitory computer readable storage medium includes algorithm for determining a total spillover spreading parameter of the fluorophore from the plurality of fluorophores where the non-transitory computer readable storage medium includes: 1) algorithm for calculating the sum of squared adjusted spillover spreading parameter values for each fluorophore; 2) algorithm for determining the square root of the sum of squared adjusted spillover spreading parameter values to generate a standard deviation or CV of the fluorophore.

In certain embodiments, the non-transitory computer readable storage medium includes algorithm for calculating a total spillover spreading parameter of a fluorophore from a generated spillover spreading matrix where the non-transitory computer readable storage medium includes: 1) algorithm for calculating a sum of squared adjusted spillover spreading values in a column corresponding to a second fluorophore and 2) algorithm for determining a square root of the sum of squared adjusted spillover spreading values in the column. In certain instances, the non-transitory computer readable storage medium includes algorithm for calculating a total spillover spreading parameter of a fluorophore from a generated spillover spreading matrix according to:

$$ColSum = \frac{1}{AgDens_{col}} \left( \sum_{row=1}^{N_{rows}} AgDens_{row}(SS_{col}^{row})^2 \right)^{1/2}$$

The non-transitory computer readable storage medium includes algorithm for identifying an optimal set of fluorophore-biomolecule reagent pairs for characterizing the sample by flow cytometry. In some embodiments, the non-transitory computer readable storage medium includes algorithm for identifying the optimal set of fluorophore-biomolecule reagent pairs with a reagent pair ranking algorithm, such as where the non-transitory computer readable storage medium includes algorithm for assigning a score to each of the fluorophore-biomolecule reagent pairs based on the calculated adjusted spillover spreading matrix value for each fluorophore-biomolecule reagent pair. In some embodiments, the non-transitory computer readable storage medium includes algorithm for identifying the optimal set of fluorophore-biomolecule reagent pairs by selecting the fluorophore-biomolecule reagent pairs having the lowest score based on the calculated adjusted spillover spreading matrix. In other embodiments, the non-transitory computer readable storage medium includes algorithm for identifying the optimal set of fluorophore-biomolecule reagent pairs by selecting the fluorophore-biomolecule reagent pairs having a score that is below a predetermined threshold based on the calculated adjusted spillover spreading matrix. In yet other embodiments, the non-transitory computer readable storage medium includes algorithm for identifying the optimal set of fluorophore-biomolecule reagent pairs by selecting at random a predetermined number of the fluorophore-biomolecule reagent pairs.

In other embodiments, the non-transitory computer readable storage medium includes algorithm for identifying the optimal set of fluorophore-biomolecule reagent pairs by applying a constrained optimization algorithm, such as where each fluorophore-biomolecule reagent pair is selected at random and subjected to a set of constraints to generate a constrained set of fluorophore-biomolecule reagent pairs. In certain embodiments, the constrained optimization algorithm includes solving a constrained optimization problem (COP). In other embodiments, the constrained optimization algorithm includes solving a constrained satisfaction problem (CSP). In certain instances, the constrained optimization algorithm includes a constraint satisfaction algorithm in which fluorophore-biomolecule reagent pairs are selected to satisfy a predetermined constraint such that each fluorophore-biomolecule reagent pair does not cause excess spillover spreading into other fluorophore-biomolecule reagent pairs in a predetermined subpopulation. In certain embodiments, the non-transitory computer readable storage medium includes algorithm for identifying the optimal set of fluorophore-biomolecule reagent pairs by applying an iterative genetic algorithm.

The non-transitory computer readable storage medium may be employed on one or more computer systems having a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

Kits

Aspects of the present disclosure further include kits, where kits include one or more of the integrated circuits described herein. In some embodiments, kits may further include programming for the subject systems, such as in the form of a computer readable medium (e.g., flash drive, USB storage, compact disk, DVD, Blu-ray disk, etc.) or instructions for downloading the programming from an internet web protocol or cloud server. Kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

UTILITY

The subject systems, methods and computer systems find use in a variety of applications where it is desirable to analyze and sort particle components in a sample in a fluid medium, such as a biological sample. In some embodiments, the systems and methods described herein find use in flow cytometry characterization of biological samples labelled with fluorescent tags. In other embodiments, the systems and methods find use in spectroscopy of emitted light. In addition, the subject systems and methods find use in increasing the obtainable signal from light collected from a sample (e.g., in a flow stream). In certain instances, the present disclosure finds use in enhancing measurement of light collected from a sample that is irradiated in a flow stream in a flow cytometer. Embodiments of the present disclosure find use where it is desirable to provide a flow cytometer with improved cell sorting accuracy, enhanced particle collection, particle charging efficiency, more accurate particle charging and enhanced particle deflection during cell sorting.

Embodiments of the present disclosure also find use in applications where cells prepared from a biological sample may be desired for research, laboratory testing or for use in therapy. In some embodiments, the subject methods and devices may facilitate obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems may facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost as compared to traditional flow cytometry systems.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method for identifying a set of fluorophore-biomolecule reagent pairs for characterizing a sample in a flow cytometer, the method comprising:
    calculating a spectral spillover spreading parameter for a plurality of fluorophores, wherein calculating the spectral spillover spreading parameter for each of the plurality of fluorophores comprises generating a matrix of fluorescence spillover spreading values for the plurality of fluorophores;
    calculating a sum of each row of the generated matrix wherein the sum of each row of the generated matrix comprises an approximation of the spectral spillover spread by each individual fluorophore into the plurality of fluorophores;
    calculating a sum of each column of the generated matrix wherein the sum of each column of the generated matrix comprises an approximation of the spectral spillover spread by the plurality of fluorophores into each individual fluorophore;
    pairing each fluorophore with a biomolecule that is specific for a biomarker of a cell in the sample to generate a plurality of fluorophore-biomolecule reagent pairs;
    generating an adjusted spillover spreading matrix for the fluorophore-biomolecule reagent pairs based on the spectral spillover spreading parameter of each fluorophore and a biomarker classification parameter; and
    identifying an optimal set of fluorophore-biomolecule reagent pairs based on the calculated spillover spreading values from the adjusted spillover spreading matrix;
    characterizing cells of the sample with the flow cytometer using the identified set of fluorophore-biomolecule reagent pairs.

2. The method according to claim 1, wherein the biomarker classification parameter comprises a quantitative population density for each biomarker in the sample.

3. The method according to claim 2, wherein the quantitative population density comprises a numerical range of the population of each biomarker in the sample.

4. The method according to claim 1, wherein the biomarker classification parameter comprises a semi-quantitative population density classification for each biomarker in the sample.

5. The method according to claim 4, wherein the semi-quantitative population density classification comprises a classification selected from the group consisting of: very high biomarker expression; high biomarker expression; medium biomarker expression; low biomarker expression and absent biomarker expression.

6. The method according to claim 1, wherein the biomarker classification parameter comprises a qualitative population density classification for each biomarker in the sample.

7. The method according to claim 6, wherein the qualitative population density classification for each biomarker in the sample is a binary biomarker classification.

8. The method according to claim 1, wherein the fluorescence spillover spreading value is calculated based on the overlap of the fluorescence spectra of the two different fluorophores.

9. The method according to claim 8, wherein calculating the spectral spillover spreading parameter for each of the plurality of fluorophores comprises:
    generating a spillover spreading matrix of fluorescence spillover spreading values for the plurality of fluorophores;
    calculating a sum of squared adjusted spillover spreading values in a column of the generated matrix; and
    determining a square root of the sum of squared adjusted spillover spreading values in the column.

10. The method according to claim 9, wherein the spectral spillover spreading parameter is calculated from the generated spillover spreading matrix according to:

$$ColSum = \frac{1}{AgDens_{col}} \left( \sum_{row=1}^{N_{rows}} AgDens_{row}(SS_{col}^{row})^2 \right)^{1/2}$$

wherein $AgDens_{col}$ is the population density value of the biomarker in each column of the spillover spreading matrix and $AgDens_{row}$ is the population density value of the biomarker in each row of the spillover spreading matrix.

11. The method according to claim 1, wherein calculating the spectral spillover spreading parameter for each of the plurality of fluorophores comprises:
    simulating spectral properties of each fluorophore; and
    calculating spillover spreading values for each of the fluorophores based on the simulated spectral properties.

12. The method according to claim 11, wherein the simulated spectral properties of the fluorophore comprises one or more of emission spectrum of the fluorophore, excitation spectrum of the fluorophore, quantum yield of the fluorophore and extinction coefficient of the fluorophore.

13. The method according to claim 1, wherein identifying a plurality of fluorophore-biomolecule reagent pairs comprises applying a constrained optimization algorithm.

14. The method according to claim 13, wherein the constrained optimization algorithm comprises solving a constrained optimization problem (COP) or a constrained satisfaction problem (CSP).

15. The method according to claim 1, wherein identifying a plurality of fluorophore-biomolecule reagent pairs comprises conducting an iterative genetic algorithm.

* * * * *